United States Patent
Takagi et al.

(10) Patent No.: US 10,830,783 B2
(45) Date of Patent: Nov. 10, 2020

(54) SAMPLE ANALYSIS SYSTEM, CLEANING LIQUID PREPARATION APPARATUS, SAMPLE ANALYZER, AND CLEANING LIQUID SUPPLY METHOD

(71) Applicant: SYSMEX CORPORATION, Kobe (JP)

(72) Inventors: Ryuki Takagi, Kobe (JP); Yuji Wakamiya, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 79 days.

(21) Appl. No.: 15/292,541

(22) Filed: Oct. 13, 2016

(65) Prior Publication Data

US 2017/0108524 A1 Apr. 20, 2017

(30) Foreign Application Priority Data

Oct. 15, 2015 (JP) ................. 2015-203672

(51) Int. Cl.
  *G01N 35/10* (2006.01)
  *G01N 35/00* (2006.01)
  *G01N 33/543* (2006.01)
(52) U.S. Cl.
  CPC ...... *G01N 35/1004* (2013.01); *G01N 33/54326* (2013.01); *G01N 35/0092* (2013.01); *G01N 35/0098* (2013.01); *G01N 35/1002* (2013.01)
(58) Field of Classification Search
  None
  See application file for complete search history.

(56) References Cited

U.S. PATENT DOCUMENTS

2005/0074363 A1 4/2005 Dunfee
2010/0216224 A1* 8/2010 Okubo ............... G01N 1/38
                                                          435/286.5
(Continued)

FOREIGN PATENT DOCUMENTS

CN        101816907 A   9/2010
JP        2008-202945 A  9/2008
(Continued)

OTHER PUBLICATIONS

Office action dated Mar. 20, 2019, in a counterpart Chinese patent application.
(Continued)

*Primary Examiner* — Kathryn Wright
(74) *Attorney, Agent, or Firm* — Metroplex IP Law Group, PLLC

(57) ABSTRACT

Disclosed is a sample analysis system comprising a cleaning liquid preparation apparatus that prepares a cleaning liquid, and a sample analyzer that comprises a measurement unit that measures a sample and a reservoir that stores the cleaning liquid prepared by the cleaning liquid preparation apparatus. The sample analyzer cleans at least a part of the measurement unit with the cleaning liquid. The cleaning liquid preparation apparatus selectively executes a first supply mode to supply the cleaning liquid to the reservoir when a liquid amount in the reservoir reaches a first amount, and a second supply mode to supply the cleaning liquid to the reservoir when the liquid amount in the reservoir reaches a second amount less than the first amount.

13 Claims, 13 Drawing Sheets

(56) References Cited

U.S. PATENT DOCUMENTS

2015/0192601 A1   7/2015  Cohen
2016/0069922 A1   3/2016  Horiuchi et al.

FOREIGN PATENT DOCUMENTS

| | | |
|---|---|---|
| JP | 2010-071897 A | 4/2010 |
| JP | 2010-151672 A | 7/2010 |
| JP | 2010-197292 A | 9/2010 |
| JP | 2010-230541 A | 10/2010 |
| JP | 2010-236916 A | 10/2010 |
| JP | 2011-007524 A | 1/2011 |
| JP | 2014-089129 A | 5/2014 |
| JP | 2015-125018 A | 7/2015 |
| WO | 2009/039122 A2 | 3/2009 |
| WO | 2009/039122 A3 | 3/2009 |
| WO | 2014/175018 A1 | 10/2014 |

OTHER PUBLICATIONS

Office action dated Aug. 23, 2019 in a counterpart Chinese patent application.
Office Action dated Oct. 23, 2019 in a counterpart Japanese patent application.
Communication pursuant to Article 94(3) EPC dated Jan. 24, 2020 in a counterpart European patent application.

\* cited by examiner

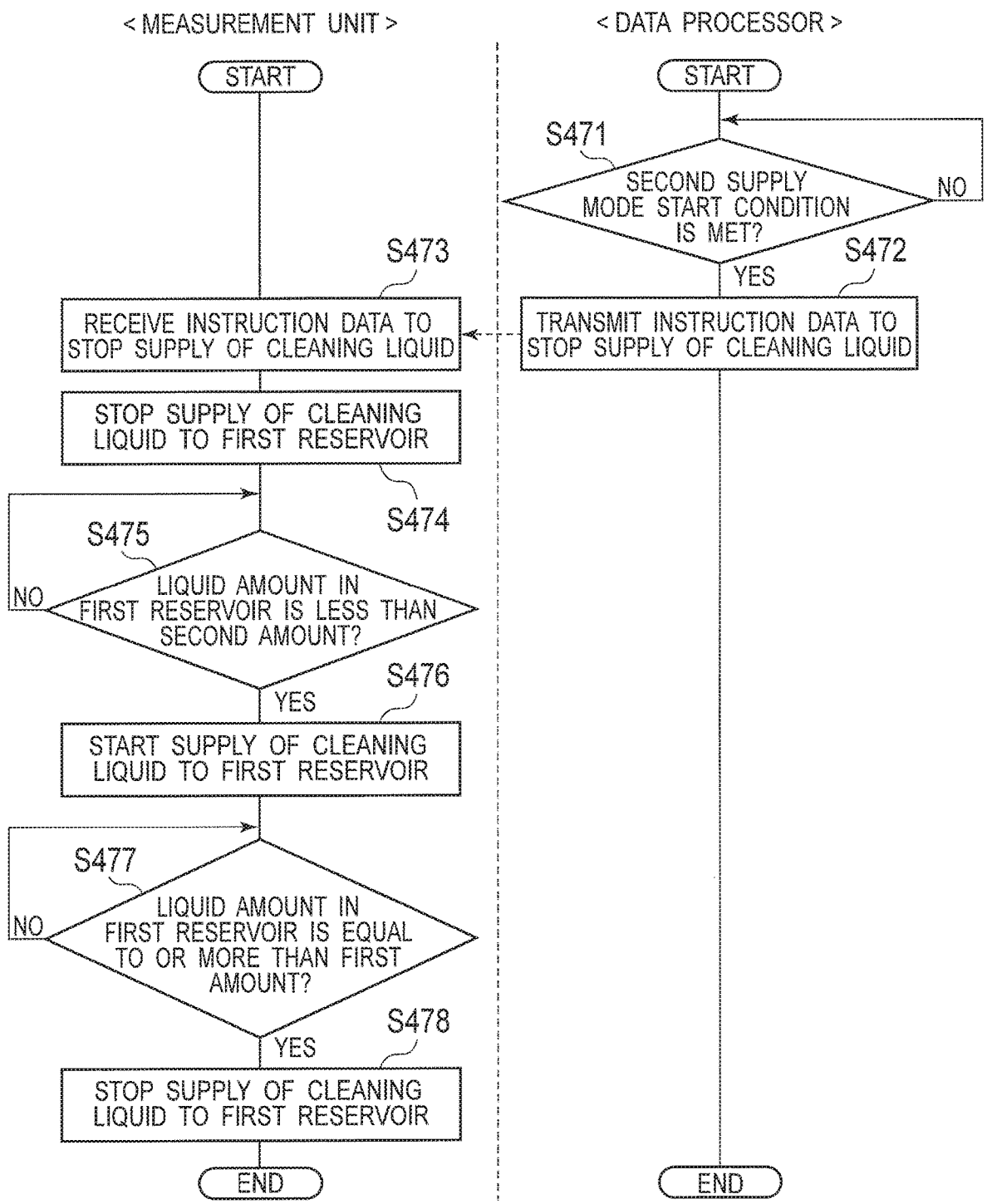

SAMPLE ANALYSIS SYSTEM, CLEANING LIQUID PREPARATION APPARATUS, SAMPLE ANALYZER, AND CLEANING LIQUID SUPPLY METHOD

CROSS REFERENCE TO RELATED APPLICATIONS

This application claims priority based on 35 USC 119 from prior Japanese Patent Application No. 2015-203672 filed on Oct. 15, 2015, entitled "SAMPLE ANALYSIS SYSTEM, CLEANING LIQUID PREPARATION APPARATUS, SAMPLE ANALYZER, AND CLEANING LIQUID SUPPLY METHOD", the entire contents of which are hereby incorporated by reference.

BACKGROUND

The disclosure relates to a sample analysis system, a cleaning liquid preparation apparatus, a sample analyzer, and a cleaning liquid supply method for supplying a cleaning liquid to the sample analyzer.

Patent Literature 1 discloses an apparatus configured to prepare a liquid to be used for cleaning of a measurement unit in a sample analyzer by mixing RO water with a high-concentration reagent. In this apparatus, the liquid prepared by mixing the RO water with the high-concentration reagent is stored in a supply chamber. The liquid stored in the supply chamber is supplied to the measurement unit and used for cleaning of the measurement unit.

Patent Literature 1: Japanese Patent Application Publication No. 2010-230541

SUMMARY

In the apparatus disclosed in Patent Literature 1, in order to quickly transfer the liquid to be used for cleaning to the measurement unit in response to a supply instruction, a float switch is provided to detect whether or not the liquid in the amount of about half the capacity of the supply chamber is housed in the supply chamber. Also, when the liquid housed in the supply chamber falls below half the capacity of the supply chamber, the liquid in the amount of about half the capacity of the supply chamber is supplied to the supply chamber. Therefore, the newly prepared liquid to be used for cleaning can account for only about half the liquid stored. It is preferable that the liquid to be used for cleaning be used for cleaning promptly after prepared. Therefore, there is a demand for an apparatus which is capable of storing a liquid to be used for cleaning such that the liquid mainly contains a newly prepared liquid, and quickly cleaning a sample analyzer with the stored liquid.

A sample analysis system according to a first aspect of embodiments includes a cleaning liquid preparation apparatus and a sample analyzer. The cleaning liquid preparation apparatus prepares a cleaning liquid. The sample analyzer includes a measurement unit configured to measure a sample and a reservoir configured to store the cleaning liquid prepared by the cleaning liquid preparation apparatus, and is configured to clean at least a part of the measurement unit with the cleaning liquid. The cleaning liquid preparation apparatus can selectively execute a first supply mode and a second supply mode. The first supply mode is a mode to supply the cleaning liquid to the reservoir when a liquid amount in the reservoir reaches a first amount. The second supply mode is a mode to supply the cleaning liquid to the reservoir when the liquid amount in the reservoir reaches a second amount less than the first amount.

A cleaning liquid preparation apparatus according to a second aspect of embodiments prepares and supplies a cleaning liquid to a sample analyzer including a measurement unit configured to measure a sample and a reservoir configured to store the cleaning liquid for cleaning at least a part of the measurement unit. The cleaning liquid preparation apparatus can selectively execute a first supply mode and a second supply mode. The first supply mode is a mode to supply the cleaning liquid to the reservoir when a liquid amount in the reservoir reaches a first amount. The second supply mode is a mode to supply the cleaning liquid to the reservoir when the liquid amount in the reservoir reaches a second amount less than the first amount.

A sample analyzer according to a third aspect of embodiments includes a measurement unit and a reservoir. The measurement unit measures a sample. The reservoir is connected to a cleaning liquid container that houses a cleaning liquid for cleaning at least a part of the measurement unit, and stores the cleaning liquid. The sample analyzer that selectively executes a first supply mode to supply the cleaning liquid to the reservoir when a liquid amount in the reservoir reaches a first amount, and a second supply mode to supply the cleaning liquid to the reservoir when the liquid amount in the reservoir reaches a second amount less than the first amount.

A cleaning liquid supply method according to a fourth aspect of embodiments includes selectively executing a first supply mode and a second supply mode. The first supply mode is a mode to supply a cleaning liquid, which is for cleaning at least a part of a measurement unit configured to measure a sample, to a reservoir configured to store the cleaning liquid when a liquid amount in the reservoir reaches a first amount. The second supply mode is a mode to supply the cleaning liquid to the reservoir when the liquid amount in the reservoir reaches a second amount less than the first amount.

One or more embodiments of a cleaning liquid supply method may comprise determining whether an apparatus is in a first supply mode or a second supply mode, in a first supply mode, supplying a cleaning liquid to a reservoir when a liquid amount in the reservoir reaches a first amount, the cleaning liquid being for cleaning at least a part of a measurement unit that measures a sample, the reservoir that stores the cleaning liquid, and in a second supply mode, supplying the cleaning liquid to the reservoir when the liquid amount in the reservoir reaches a second amount less than the first amount.

BRIEF DESCRIPTION OF DRAWINGS

FIG. 15 is a flowchart illustrating procedures of a second supply mode in Embodiment 3.

EMBODIMENTS

Figure 1:
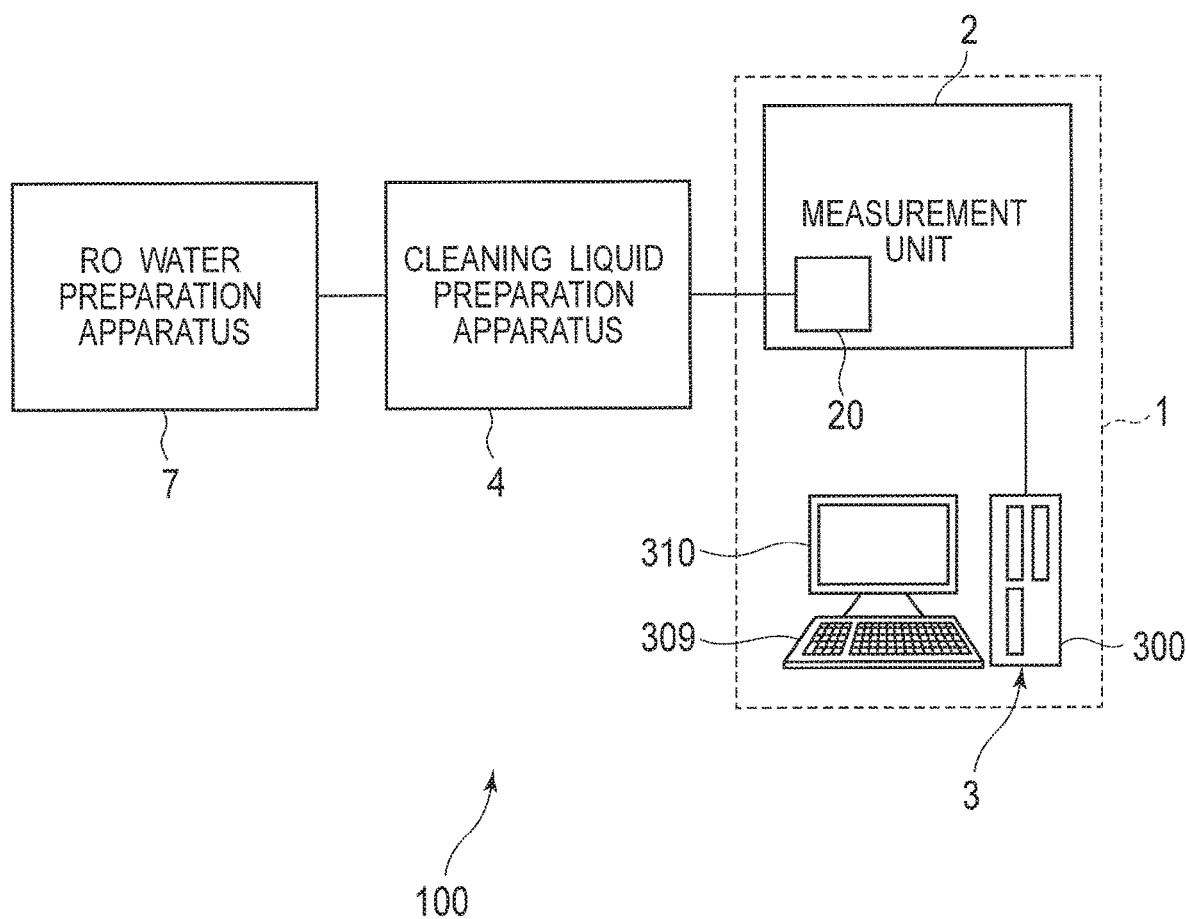
FIG. 1 is a schematic diagram illustrating a configuration of a sample analysis system according to Embodiment 1.

Embodiments are explained with referring to drawings. In the respective drawings referenced herein, the same constituents are designated by the same reference numerals and duplicate explanation concerning the same constituents is basically omitted. All of the drawings are provided to illustrate the respective examples only. No dimensional proportions in the drawings shall impose a restriction on the embodiments. For this reason, specific dimensions are the like should be interpreted with the following descriptions taken into consideration. In addition, the drawings include parts whose dimensional relationship and ratios are different from one drawing to another.

Embodiment 1

In this embodiment, description is given of a sample analysis system configured to prepare a cleaning liquid to be used for cleaning of a sample analyzer by a cleaning liquid preparation apparatus, and to supply the cleaning liquid to the sample analyzer from the cleaning liquid preparation apparatus.

<Configuration of Sample Analysis System>

With reference to FIG. 1, a configuration of a sample analysis system is described. Sample analysis system 100 includes sample analyzer 1, cleaning liquid preparation apparatus 4, and RO water preparation apparatus 7. Cleaning liquid preparation apparatus 4 is connected to sample analyzer 1 and RO water preparation apparatus 7, and prepares a cleaning liquid by using pure water (RO water) supplied from RO water preparation apparatus 7, and supplies the prepared cleaning liquid to sample analyzer 1.

Sample analyzer 1 includes measurement unit 2 and data processor 3. Measurement unit 2 measures a sample and outputs measurement data. Data processor 3 analyzes the measurement data outputted from measurement unit 2, and displays the analysis result.

Measurement unit 2 includes first reservoir 20. First reservoir 20 is a tank for storing the cleaning liquid supplied from cleaning liquid preparation apparatus 4.

Note that, in a facility with no RO water preparation apparatus 7 installed therein, a configuration of sample analysis system 100 may include no RO water preparation apparatus 7 but include sample analyzer 1 and cleaning liquid preparation apparatus 4. In this case, the system can adopt a configuration in which a pure water supply unit such as a pure water tank, which is different from RO water preparation apparatus 7, supplies pure water to cleaning liquid preparation apparatus 4.

<Configuration of Sample Analyzer>

Figure 2:
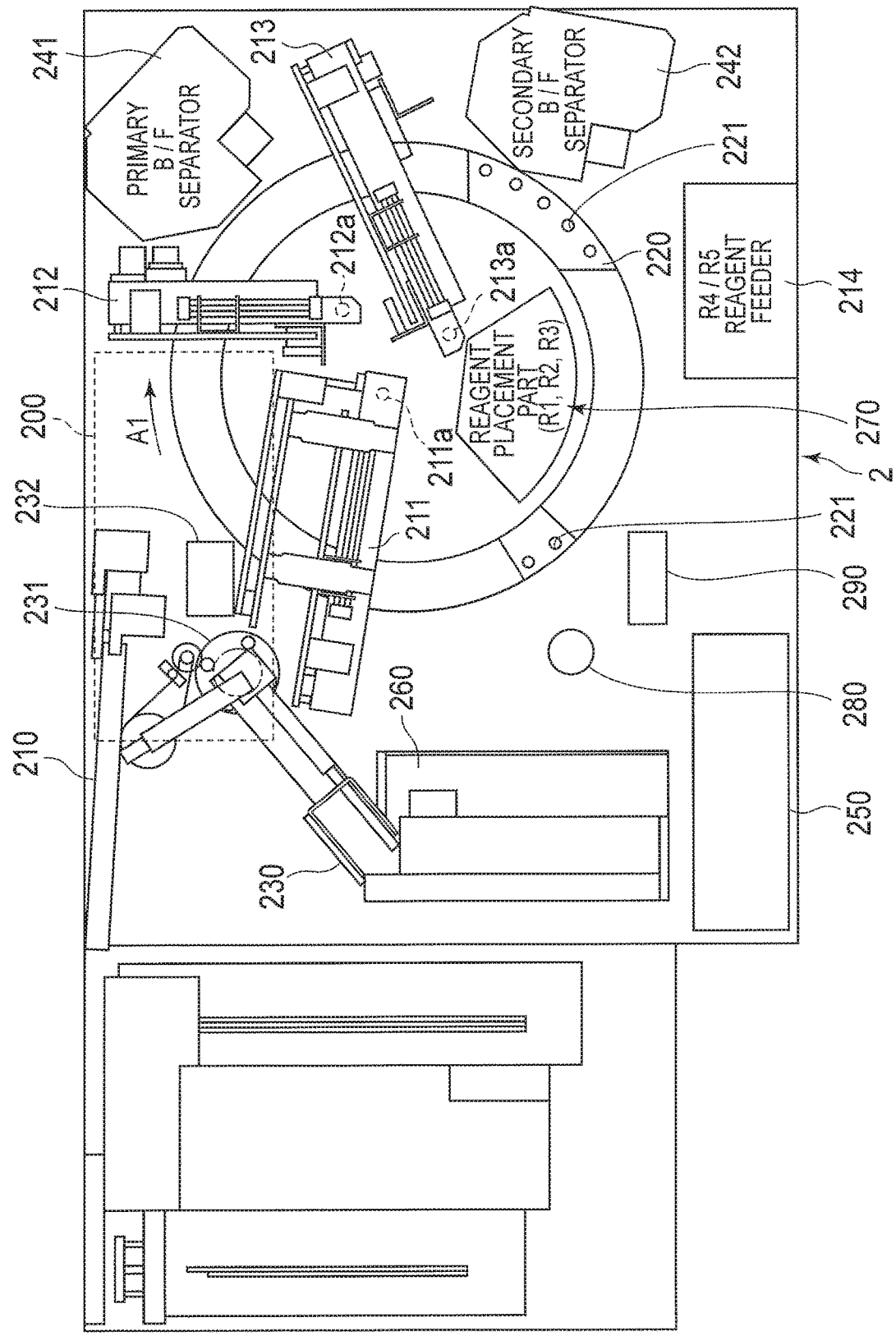
FIG. 2 is a plan view illustrating a configuration of a measurement unit.

With reference to FIG. 2, sample analyzer 1 is an immune analyzer for conducting tests for items such as hepatitis B, hepatitis C, tumor marker, and thyroid hormone by use of a sample such as blood. Sample analyzer 1 mixes a sample such as blood to be measured with a buffer solution (R1 reagent), and adds magnetic particles (R2 reagent) carrying capture antibodies, which can be bound to antigens contained in the sample, to the mixture. After the capture antibodies are bound to the antigens, sample analyzer 1 removes unreacted (free) antigens by drawing the magnetic particles to an unillustrated magnet in primary B/F (Bound Free) separator 241. Sample analyzer 1 adds labeled antibodies (R3 reagent) and, after the labeled antibodies are bound to antigens having the magnetic particles bound thereto, removes unreacted (free) labeled antibodies by drawing the bound magnetic particles to an unillustrated magnet in secondary B/F separator 242. Furthermore, after adding a dispersion liquid (R4 reagent) and a light emitting substrate (R5 reagent) which emits light during reaction process with the labeled antibodies, sample analyzer 1 measures an amount of light emitted by reaction between the labeled antibodies and the light emitting substrate. Through such a process, sample analyzer 1 quantitatively measures the antigens bound to the labeled antibodies and contained in the sample.

The cleaning liquid prepared by cleaning liquid preparation apparatus 4 is a cleaning liquid to be used for cleaning of measurement unit 2. More specifically, the cleaning liquid may be a buffer solution containing preservatives or a cleaning buffer solution such as phosphate buffered saline. Alternatively, the cleaning liquid may be a cleaning liquid with no buffering effect, but is not pure water. The cleaning liquid is prepared by diluting a high-concentration cleaning liquid with a predetermined dilution factor. Note that a diluted solution obtained by diluting the high-concentration cleaning liquid with a higher dilution factor than the cleaning liquid can be used for dilution of the sample. The R1 to R5 reagents are measurement reagents used for measurement of the sample.

Measurement unit 2 includes sample dispenser 210, R1 reagent dispenser 211, R2 reagent dispenser 212, R3 reagent dispenser 213, reaction part 220, reaction chamber feeder 230, primary B/F separator 241, secondary B/F separator 242, pipette chip feeder 250, detector 260, R4/R5 reagent feeder 214, reagent placement part 270, disposal part 280, and catcher 290. Measurement unit 2 also includes controller 200 configured to control the respective mechanisms. Controller 200 includes a CPU, a memory, and the like.

Reaction chamber feeder 230 is configured to be capable of housing reaction chambers, and sequentially feeds, one by one, the reaction chambers to sample dispensing table 231. In measurement unit 2, measurement of the sample is performed by the respective mechanisms repeating the same operation for each of consecutive turns divided by predetermined time intervals (for example, 9 seconds). Reaction chamber feeder 230 also feeds one reaction chamber in one turn. By repeating this, the reaction chambers are fed one by one. Sample dispensing table 231 includes holes capable of holding the reaction chambers in a circular pattern. Sample dispensing table 231 rotates once each turn by a predetermined angle. On sample dispensing table 231, mounting of the reaction chambers, dispensing of the R1 reagent into an empty reaction chamber, and dispensing of the sample into the reaction chamber with the R1 reagent dispensed therein are simultaneously performed for each turn.

Reagent placement part 270 is formed to have a circular shape in a planar view, and a reagent container that houses the R1 reagent, a reagent container that houses the R2 reagent, and a reagent container that houses the R3 reagent can be placed therein.

R1 reagent dispenser 211 includes probe 211*a* that is an aspiration tube. R1 reagent dispenser 211 uses probe 211*a* to aspirate the R1 reagent placed in reagent placement part 270, and dispenses the aspirated R1 reagent into the reaction chamber placed on sample dispensing table 231. R1 reagent dispenser 211 performs aspiration of the R1 reagent and dispensing thereof into the reaction chamber once each turn.

Pipette chip feeder 250 transports loaded pipette chips one by one to sample dispenser 210. Each of the pipette chips is attached to the tip of a pipette in sample dispenser 210. Pipette chip feeder 250 feeds one pipette chip in each turn.

After having the pipette chip attached thereto, sample dispenser 210 aspirates the sample from a test tube that houses the sample, and dispenses the sample into the reaction chamber having the R1 reagent dispensed therein by R1 reagent dispenser 211. Sample dispenser 210 aspirates one sample in each turn and dispenses the sample into the reaction chamber. Catcher 232 for transferring the reaction chamber is provided near sample dispensing table 231. Catcher 232 holds the reaction chamber having the sample dispensed therein on sample dispensing table 231, and mounts the reaction chamber in reaction part 220.

R2 reagent dispenser 212 includes probe 212*a* that is an aspiration tube. R2 reagent dispenser 212 uses probe 212*a* to aspirate the R2 reagent placed in reagent placement part 270, and dispenses the R2 reagent into the reaction chamber that houses the R1 reagent and the sample. R2 reagent dispenser 212 performs aspiration of the R2 reagent and dispensing thereof into the reaction chamber once each turn.

Reaction part 220 is formed into a hollow circular shape so as to surround reagent placement part 270. Also, reaction part 220 includes reaction chamber mount sections 221 arranged at predetermined intervals along the external shape thereof. Reaction chamber mount sections 221 are formed into a circular shape recessed such that the reaction chambers can be mounted therein. Moreover, reaction part 220 heats the reaction chambers set in reaction chamber mount sections 221 to about 42° C., thereby facilitating the reaction between the sample and the various reagents in the reaction chambers. Furthermore, reaction part 220 can rotate in a clockwise direction (arrow A1 direction), and moves the reaction chambers set in reaction chamber mount sections 221 to respective processing positions where various kinds of processing (dispensing of the reagents and the like) are performed. Reaction part 220 rotates in the A1 direction by an angle defined by two neighboring reaction chamber mount sections 221 in one turn.

Primary B/F separator 241 separates unreacted antigens and magnetic particles from a specimen in each of the reaction chambers. Primary B/F separator 241 pulls the reaction chamber out of reaction part 220, and agitates the sample, the R1 reagent, and the R2 reagent in the reaction chamber. Also, primary B/F separator 241 aspirates only the liquid in the reaction chamber with a pipette by drawing the magnetic particles in the reaction chamber onto a magnet. Thus, the unreacted antigens are removed from the reaction chamber. After removing the unreacted antigens, primary B/F separator 241 transfers the reaction chamber to reaction part 220.

Primary B/F separator 241 simultaneously executes, in one turn, transfer of one reaction chamber from reaction part 220, agitation of the liquid and the magnetic particles in the reaction chamber, removal of the liquid in the reaction chamber, and transfer of one reaction chamber to reaction part 220.

R3 reagent dispenser 213 includes probe 213*a* that is an aspiration tube. R3 reagent dispenser 213 uses probe 213*a* to aspirate the R3 reagent placed in reagent placement part 270. R3 reagent dispenser 213 also dispenses the R3 reagent into the reaction chamber that houses the specimen after the B/F separation by primary B/F separator 241. R3 reagent dispenser 213 performs aspiration of the R3 reagent and dispensing thereof into the reaction chamber once each turn.

Secondary B/F separator 242 transfers the reaction chamber that houses the R3 reagent and the specimen after the B/F separation by primary B/F separator 241 from reaction part 220, and separates unreacted R3 reagent (unwanted components) and the magnetic particles from the specimen in the reaction chamber. The configuration of secondary B/F separator 242 is the same as that of primary B/F separator 241, and thus description thereof is omitted.

R4/R5 reagent feeder 214 sequentially dispenses the R4 reagent and the R5 reagent into the reaction chamber that houses the specimen after the B/F separation by secondary B/F separator 242. R4/R5 reagent feeder 214 dispenses the R4 reagent into one reaction chamber in one turn, and dispenses the R5 reagent into this reaction chamber in the next turn.

Detector 260 uses a photomultiplier tube to acquire light generated through the reaction process between a light emitting substrate and labeled antibodies bound to antigens in a sample subjected to predetermined processing, thereby measuring the amount of antigens contained in the sample. Detector 260 detects an amount of antigens that is a feature amount for one sample in one turn.

Disposal part 280 includes: a hole into which the reaction chamber after detection of the amount of antigens is dropped; and a disposal bag (not illustrated) for housing the dropped reaction chamber.

Catcher 290 takes the reaction chamber out of reaction part 220, and transfers the reaction chamber to detector 260. Furthermore, catcher 290 takes the reaction chamber having the amount of antigens detected out of detector 260, and drops the reaction chamber into disposal part 280.

Controller 200 transmits amount of antigens data outputted from detector 260, as measurement data, to data processor 3.

Measurement unit 2 as described above includes a predetermined number of reaction chamber mount sections 221 in reaction part 220. In other words, the predetermined number of reaction chambers can be mounted in reaction part 220.

Moreover, sample dispenser 210, R1 reagent dispenser 211, R2 reagent dispenser 212, R3 reagent dispenser 213, and R4/R5 reagent feeder 214 are connected to first reservoir 20.

Figure 4:
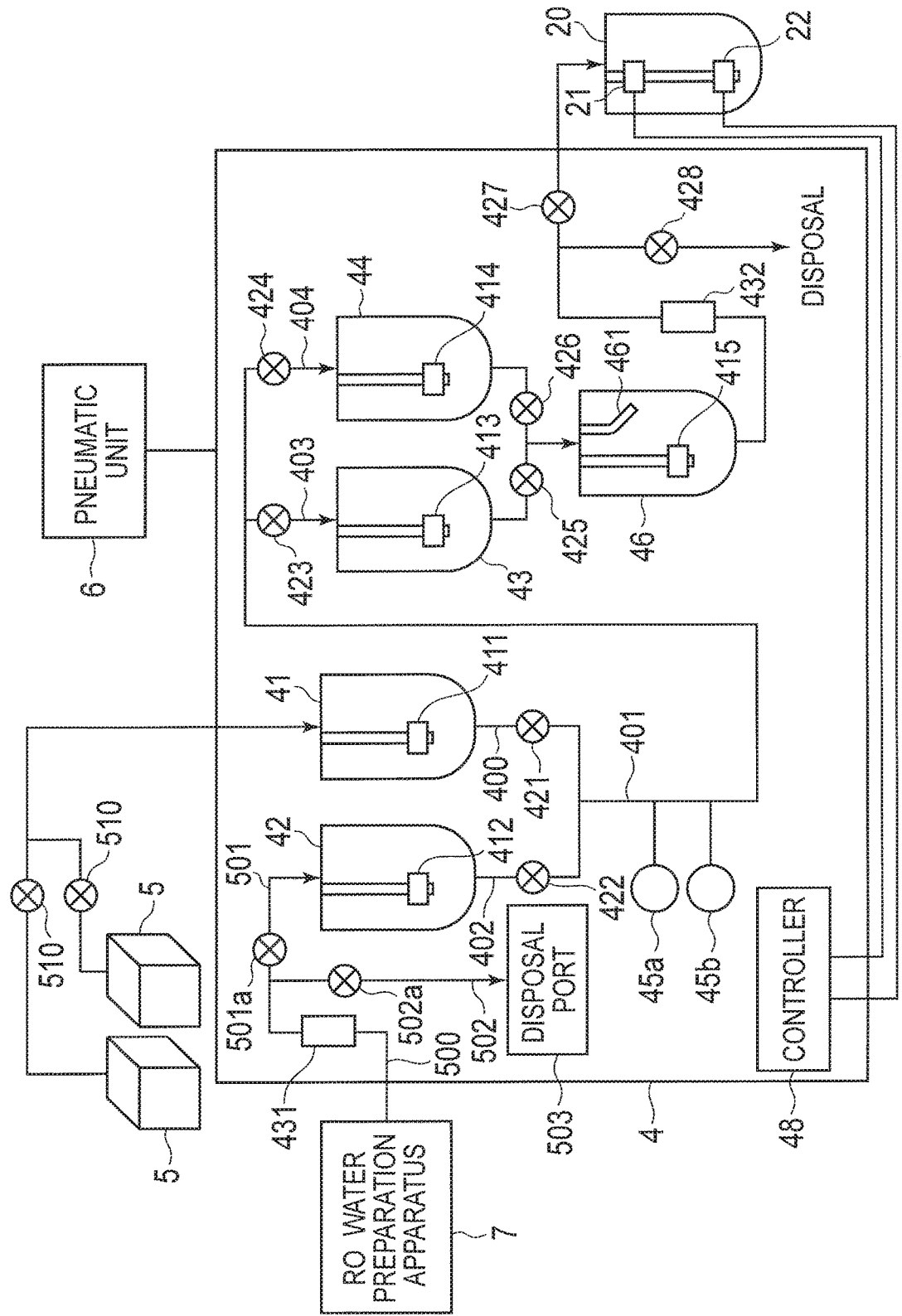
FIG. 4 is a schematic diagram illustrating a configuration of a cleaning liquid preparation apparatus.

With reference to FIG. 4, first reservoir 20 includes first detector 21 and second detector 22. First and second detectors 21 and 22 are float switches for detecting the height of the liquid level.

First detector 21 detects that a liquid amount in first reservoir 20 is less than a first amount. To be more specific, first detector 21 includes a float section, and the float section moves up and down according to the liquid amount. A detection position of first detector 21 is provided at the height where the liquid amount in first reservoir 20 is the first amount. When the float section reaches the detection position, in other words, the liquid amount is less than the first amount, first detector 21 outputs a detection signal. When the float section is above the detection position, in other words, the liquid amount is equal to or more than the first amount, first detector 21 outputs no detection signal.

Second detector 22 detects that the liquid amount in first reservoir 20 is less than a second amount. To be more specific, second detector 22 includes a float section, and the float section moves up and down according to the liquid amount. A detection position of second detector 22 is provided at the height where the liquid amount in first reservoir 20 is the second amount. When the float section reaches the detection position, in other words, the liquid amount is less than the second amount, second detector 22 outputs a detection signal. When the float section is above the detection position, in other words, the liquid amount is equal to or more than the second amount, second detector 22 outputs no detection signal.

The first amount is the amount that first reservoir 20 is close to full. For example, when first reservoir 20 has a capacity of 10 L, the first amount can be 9 L. Also, the second amount is less than the first amount. The second amount can be the amount of the cleaning liquid required for cleaning of R1 reagent dispenser 211, R2 reagent dispenser 212, and R3 reagent dispenser 213 at least for measurement of the sample that is being measured in measurement unit 2. The second amount can be the amount of the cleaning liquid required for cleaning of R1 reagent dispenser 211, R2 reagent dispenser 212, and R3 reagent dispenser 213 for measurement of a predetermined number of the sample. To be more specific, the second amount is the amount of the cleaning liquid required for cleaning of R1 reagent dispenser 211, R2 reagent dispenser 212, and R3 reagent dispenser 213, in order to dispense the R1 to R3 reagents in all the reaction chambers mounted in reaction part 220. In each turn, R1 reagent dispenser 211, R2 reagent dispenser 212, and R3 reagent dispenser 213 have their probes 211a, 212a, and 213a cleaned with the cleaning liquid. More specifically, the second amount is the amount of the cleaning liquid capable of cleaning the probes 211a, 212a, and 213a for a predetermined number of times. Note that sample dispenser 210 discards the pipette chip after each dispensing of the sample, and thus cleaning thereof is not required. Moreover, R4/R5 reagent feeder 214 dispenses the R4 reagent and the R5 reagent, which are common between the measurement items, into the reaction chamber, and thus is cleaned with a cleaning liquid less powerful than the cleaning liquid prepared by cleaning liquid preparation apparatus 4. In the following description, it is assumed that the capacity of first reservoir 20 is about 10 L, the first amount is about 9 L, and the second amount is about 3 L.

Note that the sample analyzer may be other than the immune analyzer. For example, the sample analyzer may be a blood cell analyzer, a blood coagulation analyzer, a urine particle analyzer, a biochemical analyzer, and the like. In particular, it is preferable that the sample analyzer is configured to include a circular reaction part having reaction chambers arranged therein, to dispense a sample or a specimen into the respective reaction chambers while rotating the reaction part and allow the sample or specimen to react for a predetermined period of time, and to measure the sample in the reaction chambers. In this case, a reservoir is provided in a measurement unit in the sample analyzer and the sample analyzer is configured to store a cleaning liquid prepared by a cleaning liquid preparation apparatus in the reservoir.

Figure 3:
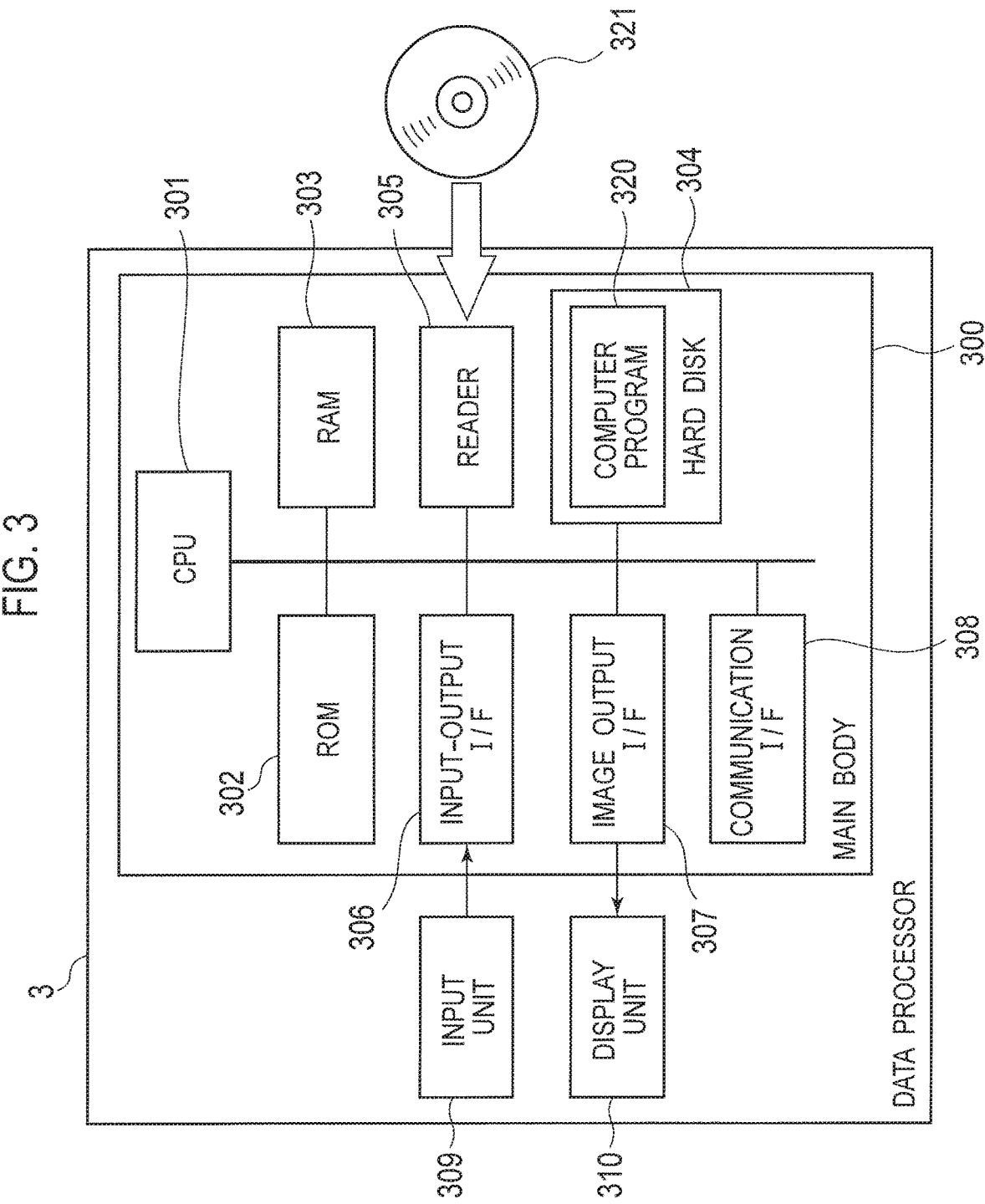
FIG. 3 is a block diagram illustrating a configuration of a data processor.

With reference to FIG. 3, a configuration of data processor 3 is described. Data processor 3 includes main body 300, input unit 309, and display unit 310. Main body 300 includes CPU (Central Processing Unit) 301, ROM (Read Only Memory) 302, RAM (Random Access Memory) 303, hard disk 304, reader 305, input-output interface 306, image output interface 307, and communication interface 308.

CPU 301 executes a computer program stored in ROM 302 and a computer program loaded onto RAM 303. RAM 303 is used to read computer programs stored in ROM 302 and hard disk 304. RAM 303 is also used as a work area for CPU 301 during execution of the computer programs.

Computer program 320 for analyzing measurement data provided from measurement unit 2 and displaying the analysis result is installed in hard disk 304.

Reader 305 is a flexible disk drive, a CD-ROM drive, a DVD-ROM drive or the like, and can read computer programs or data stored in portable storage medium 321. Also, portable storage medium 321 stores computer program 320 for causing a computer to function as data processor 3. Computer program 320 read from portable storage medium 321 is installed into hard disk 304.

Input unit 309 is connected to input-output interface 306. Display unit 310 is connected to image output interface 307. Communication interface 308 is communicably connected to measurement unit 2 and cleaning liquid preparation apparatus 4.

<Configuration of Cleaning Liquid Preparation Apparatus>

With reference to FIG. 4, cleaning liquid preparation apparatus 4 prepares a cleaning liquid by diluting a highly concentrated cleaning liquid (liquid concentrate of the cleaning liquid; hereinafter referred to as the "high-concentration cleaning liquid") to a desired concentration with RO water prepared with tap water. Here, the RO water is a kind of pure water, having impurities removed by permeating an RO (Reverse Osmosis) membrane (reverse osmosis membrane). Also, the pure water is water subjected to processing of removing impurities, including purified water, deionized water, distilled water, and the like besides the RO water.

Cleaning liquid preparation apparatus 4 includes high-concentration cleaning liquid chamber 41, RO water chamber 42, first and second dilution chambers 43 and 44, two diaphragm pumps 45a and 45b, second reservoir 46, and controller 48 configured to control operations of the respective parts in the cleaning liquid preparation apparatus 4. Controller 48 includes a CPU, a memory, and the like. Also, cleaning liquid preparation apparatus 4 is connected to two high-concentration cleaning liquid containers 5, pneumatic unit 6, and RO water preparation apparatus 7, which are provided outside the housing. Cleaning liquid preparation apparatus 4 acquires the high-concentration cleaning liquid and the RO water from high-concentration cleaning liquid containers 5 and RO water preparation apparatus 7, respectively, and uses a negative pressure and a positive pressure supplied from pneumatic unit 6 to transfer the respective liquids inside the apparatus.

Also, controller 48 is connected to first and second detectors 21 and 22 provided in first reservoir 20. First and second detectors 21 and 22 output detection signals to controller 48.

The high-concentration cleaning liquid is selectively supplied to high-concentration cleaning liquid chamber 41 from two high-concentration cleaning liquid containers 5. High-concentration cleaning liquid chamber 41 is provided with float switch 411 for detecting that a predetermined amount of high-concentration cleaning liquid is housed in the chamber. A float section of float switch 411 moves up and down according to the liquid amount. When the float section reaches the lower limit, controller 48 controls the respective parts to supply the high-concentration cleaning liquid to high-concentration cleaning liquid chamber 41 from high-concentration cleaning liquid containers 5. When the float section reaches the upper limit, controller 48 controls the respective parts to stop the supply of the high-concentration cleaning liquid to high-concentration cleaning liquid chamber 41 from high-concentration cleaning liquid containers 5. Thus, about 300 mL of high-concentration cleaning liquid is constantly stored in high-concentration cleaning liquid chamber 41.

Two high-concentration cleaning liquid containers 5 are connected to high-concentration cleaning liquid chamber 41 through electromagnetic valves 510 as switching valves, respectively. In the case of supplying the high-concentration cleaning liquid to high-concentration cleaning liquid chamber 41, controller 48 controls to open one of two electromagnetic valves 510 and close the other. Accordingly, the high-concentration cleaning liquid is supplied to high-concentration cleaning liquid chamber 41 from one of high-concentration cleaning liquid containers 5, while no high-concentration cleaning liquid is supplied from the other high-concentration cleaning liquid container 5. Therefore, while one of high-concentration cleaning liquid containers 5 is supplying the high-concentration cleaning liquid to high-concentration cleaning liquid chamber 41, the other high-concentration cleaning liquid container 5 can be replaced.

Moreover, high-concentration cleaning liquid chamber 41 is connected to flow path 401 for transferring the liquid to first dilution chamber 43 (second dilution chamber 44) from diaphragm pump 45a (45b) through flow path 400. Also, flow path 400 is provided with electromagnetic valve 421 as a switching valve. The flow of the high-concentration cleaning liquid into flow path 401 is controlled by opening and closing of electromagnetic valve 421.

RO water chamber 42 is connected to RO water preparation apparatus 7. RO water preparation apparatus 7 supplies RO water chamber 42 with RO water for diluting the high-concentration cleaning liquid.

Flow path 500 between RO water preparation apparatus 7 and RO water chamber 42 is provided with electric conductivity measurement unit 431. Electric conductivity measurement unit 431 includes a conductance meter and a temperature sensor (thermistor) to measure electric conductivity of the RO water at the position where electric conductivity measurement unit 431 is disposed. An impurity content rate and the electric conductivity of the RO water have a predetermined relationship. Thus, whether or not the impurity content rate in the RO water is not less than a specified value can be determined by measuring the electric conductivity of the RO water.

Flow path 500 between electric conductivity measurement unit 431 and RO water chamber 42 is branched off into flow path 501 for supplying the RO water to RO water chamber 42 and flow path 502 connected to disposal port 503 for discarding the RO water that has flowed in. Flow path 500 and flow path 501 are connected through supply valve 501a, while flow path 500 and flow path 502 are connected through disposal valve 502a. Therefore, when supply valve 501a is opened in a state where disposal valve 502a is closed, the RO water supplied from RO water preparation apparatus 7 flows into RO water chamber 42 through flow paths 500 and 501. On the other hand, when disposal valve 502a is opened in a state where supply valve 501a is closed, the RO water supplied from RO water preparation apparatus 7 is discarded from disposal port 503 through flow paths 500 and 502.

When the impurity content rate in the RO water sent from RO water preparation apparatus 7 is not less than the specified value, controller 48 controls supply valve 501a and disposal valve 502a to discard the RO water through a disposal flow path. On the other hand, when the impurity content rate in the RO water sent from RO water preparation apparatus 7 is less than the specified value, controller 48 controls supply valve 501a and disposal valve 502a to send the RO water to RO water chamber 42.

RO water chamber 42 is provided with float switch 412 for detecting that the RO water housed in the chamber reaches a predetermined amount (about 800 mL). A float section of float switch 412 moves up and down according to the liquid amount. When the float section reaches below a detection position corresponding to the predetermined amount (about 800 mL) in RO water chamber 42, controller 48 controls the respective parts to supply the RO water to RO water chamber 42 from RO water preparation apparatus 7. When the float section reaches the detection position or above, controller 48 controls the respective parts to stop the supply of the RO water to RO water chamber 42 from RO water preparation apparatus 7.

Moreover, RO water chamber 42 is connected to diaphragm pumps 45a and 45b on flow path 402 through electromagnetic valve 422 as a switching valve.

First and second dilution chambers 43 and 44 are used to dilute the high-concentration cleaning liquid with the RO water. As described later, first and second dilution chambers 43 and 44 can each house about 300 mL of liquid (mixture of the high-concentration cleaning liquid and the RO water) sent by diaphragm pumps 45a and 45b. First and second dilution chambers 43 and 44 are provided with vertically movable float switches 413 and 414 for each detecting that the remaining amount of the liquid (mixture of the high-concentration cleaning liquid and the RO water) housed in the corresponding chamber reaches approximately zero. Moreover, first dilution chamber 43 (second dilution chamber 44) is connected to flowpath 401 by flowpath 403 (404) through electromagnetic valve 423 (424) as a switching valve. By controlling opening and closing of electromagnetic valves 423 and 424, it can be selected whether the liquid (the RO water and the high-concentration cleaning liquid) transferred through flow path 401 is supplied to first dilution chamber 43 from flow path 403 or to second dilution chamber 44 from flow path 404. First dilution chamber 43 (second dilution chamber 44) is connected to second reservoir 46 through electromagnetic valve 425 (426) as a switching valve.

Diaphragm pumps 45a and 45b are configured to perform the same operation at the same time. Diaphragm pump 45a (45b) measures about 6.0 mL (constant amount) of high-concentration cleaning liquid and RO water in one quantitative operation, and supplies about 12 mL (about 6.0 mL×2) of liquid in total through one quantitative operation.

Second reservoir 46, or a tank, is configured to be capable of housing about 300 mL of liquid. Also, second reservoir 46 is used to store the liquid (mixture of the high-concentration cleaning liquid and the RO water) selectively supplied from first and second dilution chambers 43 and 44, and to agitate the liquid. To be more specific, second reservoir 46 includes a bent pipe 461, and the high-concentration cleaning liquid and the RO water are agitated by a convective flow generated by the liquid (mixture of the high-concentration cleaning liquid and the RO water), which is supplied from first and second dilution chambers 43 and 44, flowing along the inner wall surface of second reservoir 46.

Second reservoir 46 is provided with a vertically movable float switch 415 for detecting that the remaining amount of the liquid (mixture of the high-concentration cleaning liquid and the RO water) housed in the chamber reaches approximately zero. When the liquid is transferred from first dilution chamber 43 to second reservoir 46, controller 48 opens electromagnetic valve 425 and closes electromagnetic valve 426. Thus, about 300 mL of liquid (mixture of the high-concentration cleaning liquid and the RO water) is supplied to second reservoir 46 from first dilution chamber 43. On the other hand, when the liquid is transferred from second dilution chamber 44 to second reservoir 46, controller 48 opens electromagnetic valve 426 and closes electromagnetic valve 425. Thus, about 300 mL of liquid (mixture of the high-concentration cleaning liquid and the RO water) is supplied to second reservoir 46 from second dilution chamber 44.

Second reservoir 46 agitates the mixture of high-concentration cleaning liquid and RO water to prepare a cleaning liquid diluted to a desired concentration, for example, 25 times dilution. Second reservoir 46 is connected to first reservoir 20 provided in measurement unit 2 through supply part 427 that is a switching valve. Supply part 427 is an electromagnetic valve. Controller 48 controls supply part 427 to supply the cleaning liquid of the desired concentration from second reservoir 46 to first reservoir 20. To be more specific, controller 48 controls the respective parts including supply part 427 to supply about 300 mL (total amount of cleaning liquid prepared in one preparation operation in second reservoir 46) of cleaning liquid of the desired concentration each time to first reservoir 20 from second reservoir 46.

Electric conductivity measurement unit 432 is provided between second reservoir 46 and supply part 427. Electric conductivity measurement unit 432 includes a conductance meter and a temperature sensor (thermistor) to measure electric conductivity of the cleaning liquid at the position where electric conductivity measurement unit 432 is disposed. The concentration and the electric conductivity of the cleaning liquid have a predetermined relationship. Thus, the concentration of the prepared cleaning liquid can be determined by measuring the electric conductivity of the cleaning liquid (mixture) obtained by mixing the high-concentration cleaning liquid with the RO water. Also, a disposal flow path is connected between electric conductivity measurement unit 432 and supply part 427 through electromagnetic valve 428. When the measured concentration of the cleaning liquid is not the desired concentration, the cleaning liquid is discarded through the disposal flow path.

A rate of preparation of the cleaning liquid by cleaning liquid preparation apparatus 4 is about 10 L/hour.

<Operations of Sample Analysis System>

Next, description is given of operations of sample analysis system 100 according to the embodiment.

When an instruction to start measurement is given to sample analyzer 1, measurement unit 2 executes a sample measurement operation. In the sample measurement operation, controller 200 controls the respective parts, and measurement unit 2 measures a sample as described below.

With reference to FIG. 2, reaction chamber feeder 230 feeds one reaction chamber per turn onto sample dispensing table 231. R1 reagent dispenser 211 aspirates the R1 reagent placed in reagent placement part 270, and dispenses the R1 reagent once per turn into the reaction chamber placed on sample dispensing table 231. Pipette chip feeder 250 feeds one pipette chip per turn to sample dispenser 210, and sample dispenser 210 wears the pipette chip. Then, sample dispenser 210 aspirates the sample from a test tube, and dispenses the sample once per turn into the reaction chamber with the R1 reagent housed therein. Thereafter, catcher 232 transfers one reaction chamber per turn to reaction part 220 from sample dispensing table 231.

R2 reagent dispenser 212 aspirates the R2 reagent placed in reagent placement part 270, and dispenses the R2 reagent once per turn into the reaction chamber placed in reaction part 220. Reaction part 220 rotates in the A1 direction by a predetermined angle once per turn. The reaction chamber having the R2 reagent dispensed therein is rotated for a predetermined period of time in reaction part 220 and reaches a predetermined first ejection position. Primary B/F separator 241 takes out the reaction chamber at the first ejection position once per turn, and transfers the reaction chamber to a predetermined hold position. Primary B/F separator 241 agitates the liquid and magnetic particles in the reaction chamber placed at the hold position once per turn. Primary B/F separator 241 aspirates the liquid from the reaction chamber once per turn to remove unreacted antigens. Primary B/F separator 241 transfers, once per turn, the reaction chamber having unreacted magnetic particles removed therefrom to a predetermined first mount position in reaction part 220 from the hold position.

R3 reagent dispenser 213 aspirates the R3 reagent placed in reagent placement part 270, and dispenses the R3 reagent once per turn into the reaction chamber returned to reaction part 220 from primary B/F separator 241. The reaction chamber having the R3 reagent dispensed therein is rotated for a predetermined period of time in reaction part 220 and reaches a predetermined second ejection position. Secondary B/F separator 242 takes out the reaction chamber at the second ejection position once per turn, and transfers the reaction chamber to a predetermined hold position. Secondary B/F separator 242 agitates the liquid and magnetic particles in the reaction chamber placed at the hold position once per turn. Secondary B/F separator 242 aspirates the liquid from the reaction chamber once per turn to remove unwanted components. Secondary B/F separator 242 transfers, once per turn, the reaction chamber having the unwanted components removed therefrom to a predetermined second mount position in reaction part 220 from the hold position.

R4/R5 reagent feeder 214 dispenses the R4 reagent once per turn to the reaction chamber returned to reaction part 220 from secondary B/F separator 242, and dispenses the R5 reagent to the same reaction chamber in the next turn. The reaction chamber having the R4 and R5 reagents dispensed therein is rotated for a predetermined period of time in reaction part 220 and reaches a predetermined third ejection position. Then, catcher 290 transfers the reaction chamber that reaches the third ejection position to detector 260. Detector 260 detects the amount of antigens in the sample. Catcher 290 takes out the reaction chamber from detector 260 after the measurement, and discards the reaction chamber into disposal part 280.

Controller 200 transmits measurement data to data processor 3, the measurement data indicating the amount of antigens in the sample detected by detector 260. Data processor 3 analyzes the measurement data and displays the analysis result on display unit 310.

In the measurement operation as described above, sample dispenser 210, R1 reagent dispenser 211, R2 reagent dispenser 212, R3 reagent dispenser 213, and R4/R5 reagent feeder 214 use the cleaning liquid stored in first reservoir 20 to execute a cleaning operation to clean the flow path of the liquid in each turn. R1 reagent dispenser 211, R2 reagent dispenser 212, and R3 reagent dispenser 213 have their probes 211a, 212a, and 213a cleaned with the cleaning liquid. Note that, for removal of the unreacted antigens, primary B/F separator 241 and secondary B/F separator 242 can clean the magnetic particles with a cleaning liquid different from the cleaning liquid described above. A rate of consumption of the cleaning liquid in first reservoir 20 by measurement unit 2 is about 9 L/hour.

Figure 5:
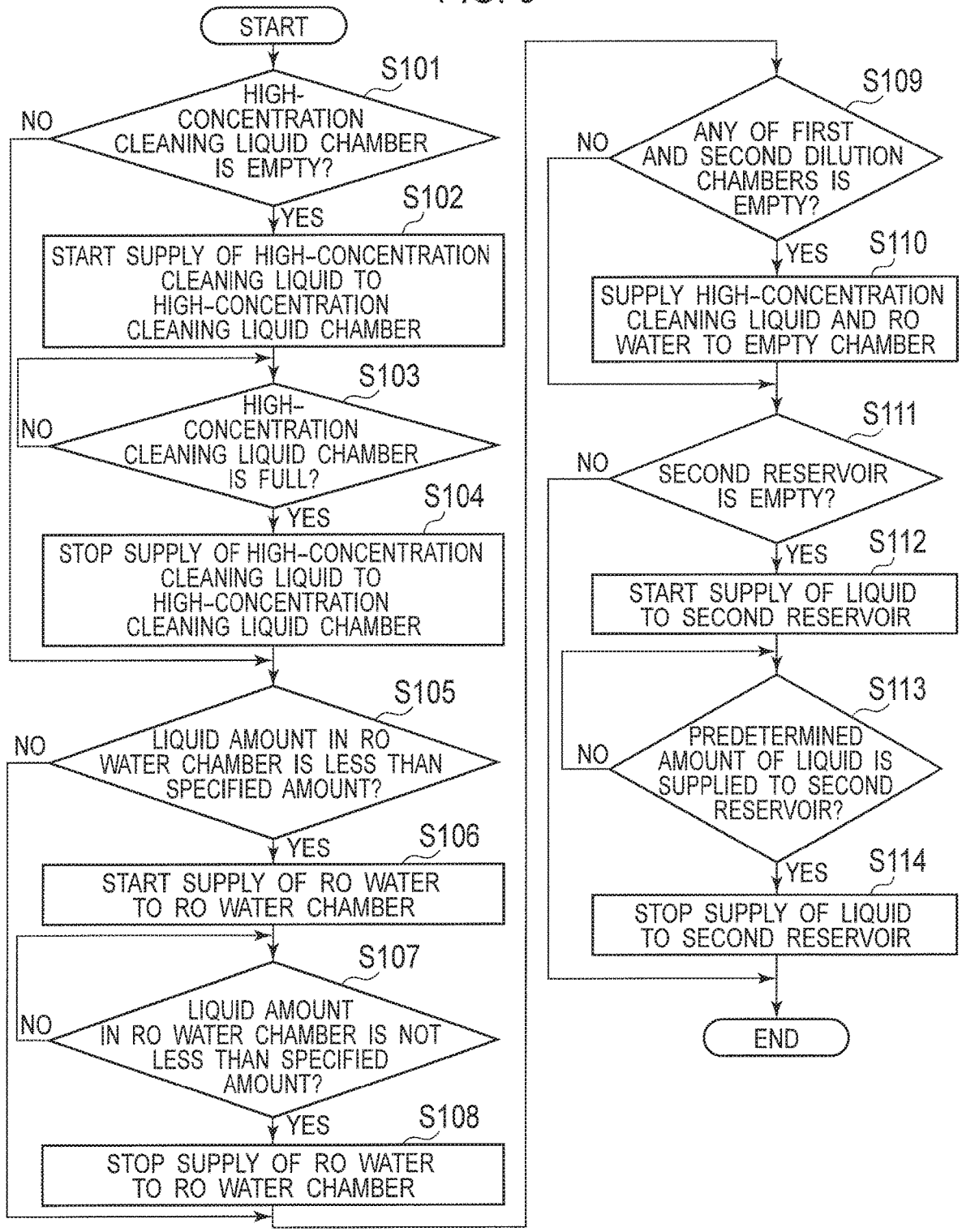
FIG. 5 is a flowchart illustrating procedures of a cleaning liquid preparation operation.

With reference to FIG. 5, description is given of a cleaning liquid preparation operation by cleaning liquid preparation apparatus 4.

Controller 48 determines whether or not high-concentration cleaning liquid chamber 41 is empty based on an output signal from float switch 411 (Step S101). When high-concentration cleaning liquid chamber 41 is empty, that is, the float section of float switch 411 reaches the lower limit (YES in Step S101), controller 48 opens one of electromagnetic valves 510 and closes the other, thereby starting the supply of the high-concentration cleaning liquid to high-concentration cleaning liquid chamber 41 from one of high-concentration cleaning liquid containers 5 (Step S102). On the other hand, when high-concentration cleaning liquid chamber 41 is not empty (NO in Step S101), controller 48 moves the processing to Step S105.

Controller 48 determines whether or not high-concentration cleaning liquid chamber 41 is full based on the output signal from float switch 411 (Step S103). When high-concentration cleaning liquid chamber 41 is filled up, that is, the float section of float switch 411 reaches the upper limit (YES in Step S103) as a result of the supply of the high-concentration cleaning liquid to high-concentration cleaning liquid chamber 41, controller 48 closes the electromagnetic valve 510 in the opened state, thereby stopping the supply of the high-concentration cleaning liquid (Step S104). Thus, about 300 mL of high-concentration cleaning liquid is stored in high-concentration cleaning liquid chamber 41. When high-concentration cleaning liquid chamber 41 is not full (NO in Step S103), controller 48 repeats the processing of Step S103.

Then, controller 48 determines whether or not the liquid amount in RO water chamber 42 is less than a specified amount (about 800 mL) based on an output signal from float switch 412 (Step S105). When the liquid amount in RO water chamber 42 is less than the specified amount (YES in Step S105), controller 48 opens supply valve 501a to start the supply of RO water to RO water chamber 42 from RO water preparation apparatus 7 (Step S106). When the liquid amount in RO water chamber 42 is not less than the specified amount (NO in Step S105), controller 48 moves the processing to Step S109.

Controller 48 determines whether or not the liquid amount in RO water chamber 42 is not less than the specified amount (about 800 mL) based on the output signal from float switch 412 (Step S107). When the liquid amount in RO water chamber 42 is not less than the specified amount (YES in Step S107), controller 48 closes supply valve 501a in the opened state, thereby stopping the supply of RO water (Step S108). Thus, about 800 mL of RO water is stored in RO water chamber 42. When the liquid amount in RO water chamber 42 is yet to reach the specified amount (about 800 mL) (NO in Step S107), controller 48 repeats the processing of Step S107.

Controller 48 determines whether or not any of first and second dilution chambers 43 and 44 is empty based on the output signals from float switches 413 and 414 (Step S109). When any of first and second dilution chambers 43 and 44 is empty, that is, the float section of float switch 413 or 414 reaches the lower limit (YES in Step S109), controller 48 controls diaphragm pumps 45a and 45b to supply a predetermined amount of high-concentration cleaning liquid and RO water to the empty one of first and second dilution chambers 43 and 44 (Step S110). In this event, 12 mL of RO water is supplied 24 times and 12 mL of high-concentration cleaning liquid is supplied once. In other words, the high-concentration cleaning liquid is diluted 25 times with the RO water. When none of first and second dilution chambers 43 and 44 is empty (NO in Step S109), controller 48 moves the processing to Step S111.

Controller 48 determines whether or not second reservoir 46 is empty based on an output signal from float switch 415 (Step S111). When second reservoir 46 is empty, that is, the float section of float switch 415 reaches the lower limit (YES in Step S111), controller 48 controls electromagnetic valves 425 and 426 to start the supply of the liquid to second reservoir 46 from one of first and second dilution chambers 43 and 44 (Step S112).

Controller 48 determines whether or not a predetermined amount (about 300 mL) of liquid is supplied to second reservoir 46 (Step S113). In this processing, controller 48 determines whether or not the total amount (about 300 mL) of liquid is supplied to second reservoir 46 from one of first and second dilution chambers 43 and 44 based on an output signal from float switches 413 and 414. When the predetermined amount of liquid is supplied to second reservoir 46 (YES in Step S113), controller 48 controls electromagnetic valves 425 and 426 to stop the supply of the liquid to second reservoir 46 (Step S114) and then terminates the processing. The supplied liquid is agitated in second reservoir 46, and thus about 300 mL of cleaning liquid of the desired concentration is stored in second reservoir 46. When the predetermined amount of liquid is not supplied yet to second reservoir 46 (NO in Step S113), controller 48 repeats the processing of Step S113.

Cleaning liquid preparation apparatus 4 repeatedly executes the cleaning liquid preparation operation as described above, thereby setting a state where the liquid is stored in high-concentration cleaning liquid chamber 41, RO water chamber 42, first dilution chamber 43, second dilution chamber 44, and second reservoir 46.

<First Supply Mode>

With the consumption of the cleaning liquid in measurement unit 2, cleaning liquid preparation apparatus 4 executes a first supply mode as described below.

Figure 6:
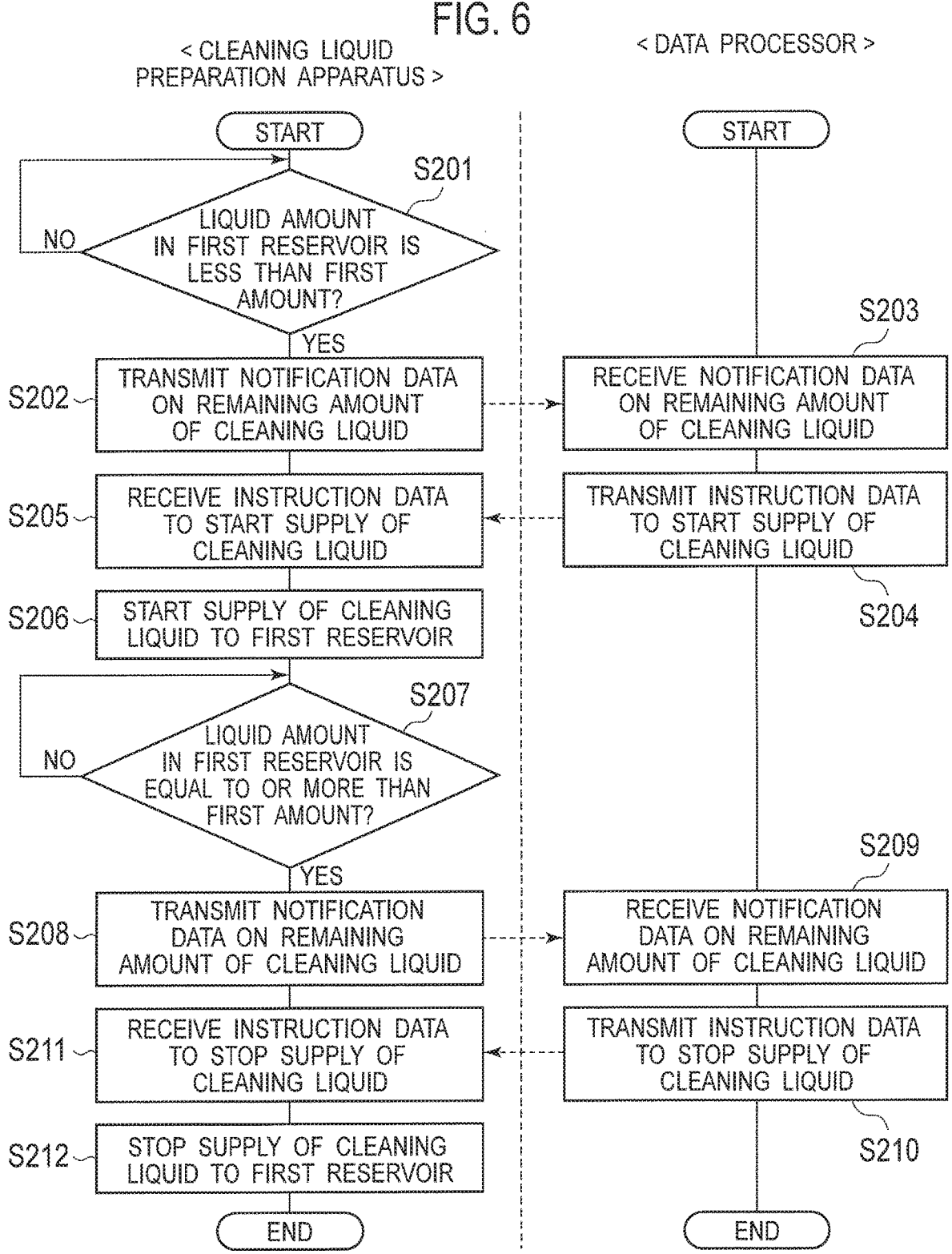
FIG. 6 is a flowchart illustrating procedures of a first supply mode in Embodiment 1.

With reference to FIG. 6, the first supply mode is described.

In the first supply mode, controller 48 determines whether or not the liquid amount in first reservoir 20 is less than the first amount, based on an output signal from first detector 21 (Step S201). When the liquid amount in first reservoir 20 is equal to or more than the first amount, that is, no detection signal is outputted from first detector 21 (NO in Step S201), controller 48 repeats the processing of Step S201.

When the liquid amount in first reservoir 20 is less than the first amount, that is, the detection signal is outputted from first detector 21 (YES in Step S201), controller 48 transmits notification data for notifying that the remaining amount of cleaning liquid is less than the first amount to data processor 3 (Step S202).

When data processor 3 receives the notification data on the remaining amount of cleaning liquid (Step S203), CPU 301 transmits instruction data to instruct to start the supply of the cleaning liquid to cleaning liquid preparation apparatus 4 (Step S204).

Figure 7A:
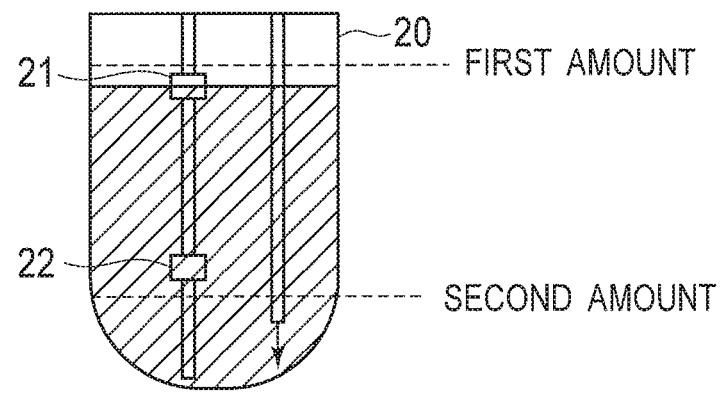
FIG. 7A is a diagram for explaining supply of a cleaning liquid to a first reservoir.

When cleaning liquid preparation apparatus 4 receives the instruction data to start the supply of the cleaning liquid (Step S205), controller 48 opens supply part 427 to start the supply of the cleaning liquid to first reservoir 20 from second reservoir 46 (Step S206). As illustrated in FIG. 7A, when the liquid amount in first reservoir 20 falls below the first amount, the supply of the cleaning liquid to first reservoir 20 is started.

Controller 48 determines whether or not the liquid amount in first reservoir 20 is equal to or more than the first amount, based on the output signal from first detector 21 (Step S207). When the liquid amount in first reservoir 20 is less than first amount, that is, the detection signal is outputted from first detector 21 (NO in Step S207), controller 48 repeats the processing of Step S207. Thus, the supply of the cleaning liquid from second reservoir 46 to first reservoir 20 is carried on.

When the liquid amount in first reservoir 20 reaches the first amount or more, that is, no more detection signal is outputted from first detector 21 (YES in Step S207), controller 48 transmits notification data for notifying that the remaining amount of cleaning liquid reaches the first amount or more to data processor 3 (Step S208).

When data processor 3 receives the notification data on the remaining amount of cleaning liquid (Step S209), CPU 301 transmits instruction data to instruct to stop the supply of the cleaning liquid to cleaning liquid preparation apparatus 4 (Step S210), and then terminates the processing.

Figure 7B:
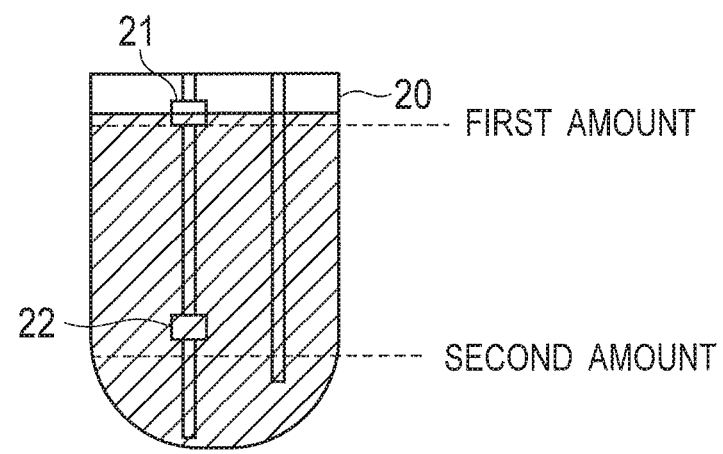
FIG. 7B is a diagram for explaining supply of a cleaning liquid to the first reservoir.

When cleaning liquid preparation apparatus 4 receives the instruction data to stop the supply of the cleaning liquid (Step S211), controller 48 closes supply part 427 to stop the supply of the cleaning liquid to first reservoir 20 from second reservoir 46 (Step S212), and then terminates the processing. As illustrated in FIG. 7B, when the liquid amount in first reservoir 20 reaches the first amount or more, the supply of the cleaning liquid to first reservoir 20 is stopped.

In the first supply mode, when the liquid amount in first reservoir 20 falls below the first amount (about 9 L), the supply of the cleaning liquid to first reservoir 20 is started. More specifically, the liquid amount in first reservoir 20 is slightly (for example, about several mL to several tens mL) less than the first amount when the supply of the cleaning liquid to first reservoir 20 is started. Also, the cleaning liquid is supplied until the liquid amount in first reservoir 20 reaches the first amount or more. Therefore, the amount of cleaning liquid to be supplied corresponds to a difference between the first amount and the liquid amount in first reservoir 20 at the start of the supply of cleaning liquid. Therefore, in the first supply mode, when the liquid amount in first reservoir 20 falls below the first amount (about 9 L), the cleaning liquid is supplied to first reservoir 20 in an amount less than the first amount.

Cleaning liquid preparation apparatus 4 can maintain the liquid amount in first reservoir 20 at the first amount (about 9 L) by repeatedly executing the supply of the cleaning liquid in the first supply mode as described above.

Note that, when the liquid amount in first reservoir 20 falls below the first amount, controller 48 may open supply part 427 to supply the cleaning liquid to first reservoir 20 from second reservoir 46 without sending notification data to data processor 3. On the other hand, when the liquid amount in first reservoir 20 reaches the first amount or more, controller 48 may close supply part 427 to stop the supply of the cleaning liquid to first reservoir 20 from second reservoir 46 without sending notification data to data processor 3.

<Second Supply Mode>

As the first supply mode as described above is continuously executed, the old cleaning liquid is likely to stay behind since the liquid amount in first reservoir 20 does not fall significantly less than the first amount. Therefore, cleaning liquid preparation apparatus 4 executes a second supply mode as described below.

Cleaning liquid preparation apparatus 4 executes the second supply mode when a preset condition is met. Hereinafter, such a preset condition is referred to as the "second supply mode start condition" or the "second supply mode execution condition". The second supply mode start condition can be that communication between data processor 3 and cleaning liquid preparation apparatus 4 is established after sample analyzer 1 is activated. Alternatively, the second supply mode start condition can also be that the date of an internal clock in data processor 3 changes to the next date. Alternatively, the second supply mode start condition can also be that a time previously set by a user arrives. Note that a condition other than those described above can also be set as the second supply mode start condition.

Figure 8:
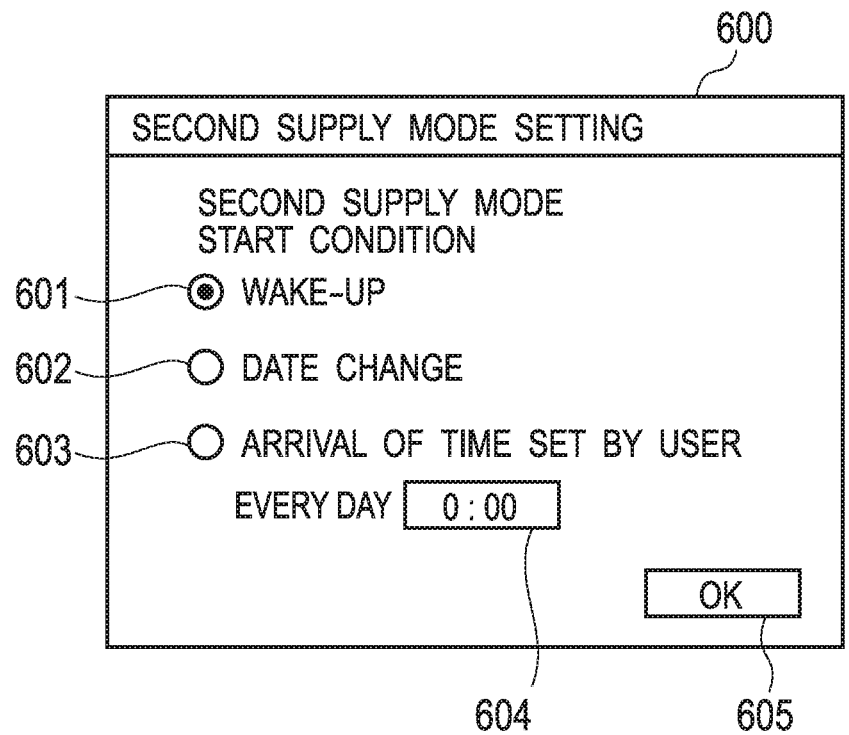
FIG. 8 is a diagram illustrating a setting screen for a second supply mode start condition.

In this embodiment, the user can use data processor 3 to set the second supply mode start condition. Here, FIG. 8 is referred to. Data processor 3 can display a setting screen for setting a condition for executing the second supply mode. As illustrated in FIG. 8, setting screen 600 includes three selectors 601, 602, and 603. Selectors 601 to 603 are radio buttons.

Selector 601 is used to set the second supply mode execution condition that sample analyzer 1 wakes up. Here, the wake-up of sample analyzer 1 is the point when the communication between data processor 3 and cleaning liquid preparation apparatus 4 is established after the activation of sample analyzer 1.

Selector 602 is used to set the second supply mode execution condition that the date of the internal clock in data processor 3 changes to the next date.

Selector 603 is used to set the second supply mode execution condition that a time previously set by the user arrives. Setting screen 600 also includes specification section 604. Specification section 604 is used by the user to specify the time. The time specified using specification section 604 is the time to execute the second supply mode.

The user selects any one of selectors 601 to 603 on setting screen 600. When selecting selector 603, the user specifies the time to execute the second supply mode in specification section 604. When the setting of the second supply mode execution condition is completed, the user selects OK button 605 to close setting screen 600. Thus, the setting information is stored in hard disk 304.

Note that controller 48 in cleaning liquid preparation apparatus 4 may be configured to be able to set the second supply mode start condition. In this case, the second supply mode start condition can be that cleaning liquid preparation apparatus 4 is activated. Alternatively, the second supply mode start condition can also be that the date of an internal clock in controller 48 changes to the next date. Alternatively, the second supply mode start condition can also be that a time previously set by the user arrives. Note that a condition other than those described above can also be set as the second supply mode start condition.

Next, an operation of activating sample analyzer 1 is described. Data processor 3 can set automatic wake-up. The user sets a time to execute the automatic wake-up on an unillustrated setting screen for the automatic wake-up. When the time to execute the automatic wake-up is set, sample analyzer 1 is automatically activated at this time. Alternatively, when no automatic wake-up is set, sample analyzer 1 is manually activated.

Figure 9:
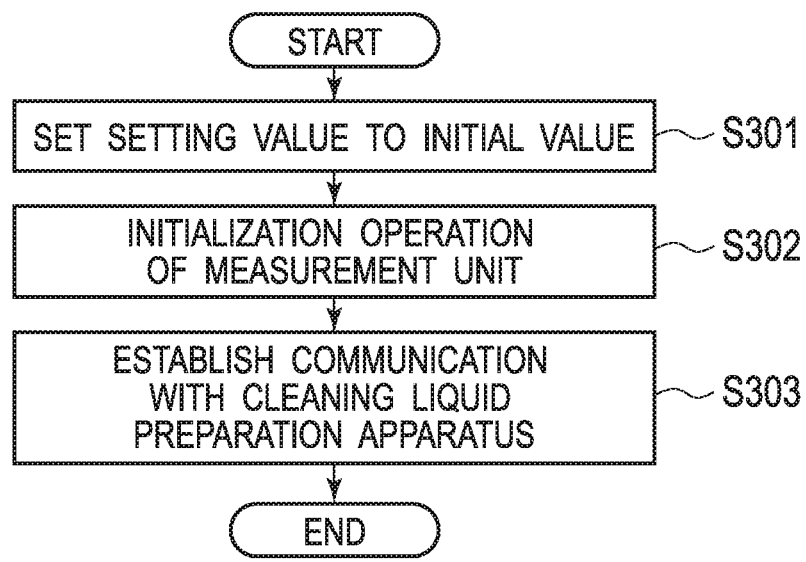
FIG. 9 is a flowchart illustrating procedures of an operation of activating sample analyzer 1.

With reference to FIG. 9, in the operation of activating sample analyzer 1, CPU 301 sets various set values to initial values (Step S301). Next, CPU 301 causes measurement unit 2 to execute an initialization operation such as locating the respective parts at initial positions (Step S302), and executes processing of establishing communication with cleaning liquid preparation apparatus 4 (Step S303). In the communication establishment processing, CPU 301 transmits and receives predetermined data to and from cleaning liquid preparation apparatus 4. When the communication with cleaning liquid preparation apparatus 4 is established, CPU 301 terminates the processing.

Next, description is given of dating processing by sample analyzer 1. The dating processing is processing of determining the time to start a day in sample analyzer 1. Data processor 3 includes the internal clock and thus can acquire the current time. In the dating processing, the user can set what time (for example, 2:30 am or the like) of actual time (local time of data processor 3, which is generally set to Japan Standard Time in Japan) on the internal clock is set as the commencement of a day. Hereinafter, the time set as the commencement of a day is referred to as the "date change time".

In many facilities, sample analyzer 1 is activated once a day. Therefore, in such facilities, the second supply mode can be executed once a day by executing the second supply mode when the communication is established between data processor 3 and cleaning liquid preparation apparatus 4. In the second supply mode, more old cleaning liquid than that in the first supply mode is replaced with new cleaning liquid. Therefore, by executing the second supply mode once a day, a large amount of old cleaning liquid can be replaced with new cleaning liquid once a day. Moreover, in a facility that keeps sample analyzer 1 running over several days, a large amount of old cleaning liquid can be replaced with new cleaning liquid once a day by executing the second supply mode when the time reaches the date change time. Moreover, the sample analyzer can also respond to other operations by enabling the second supply mode to be executed when a time previously set by the user arrives.

Figure 10:
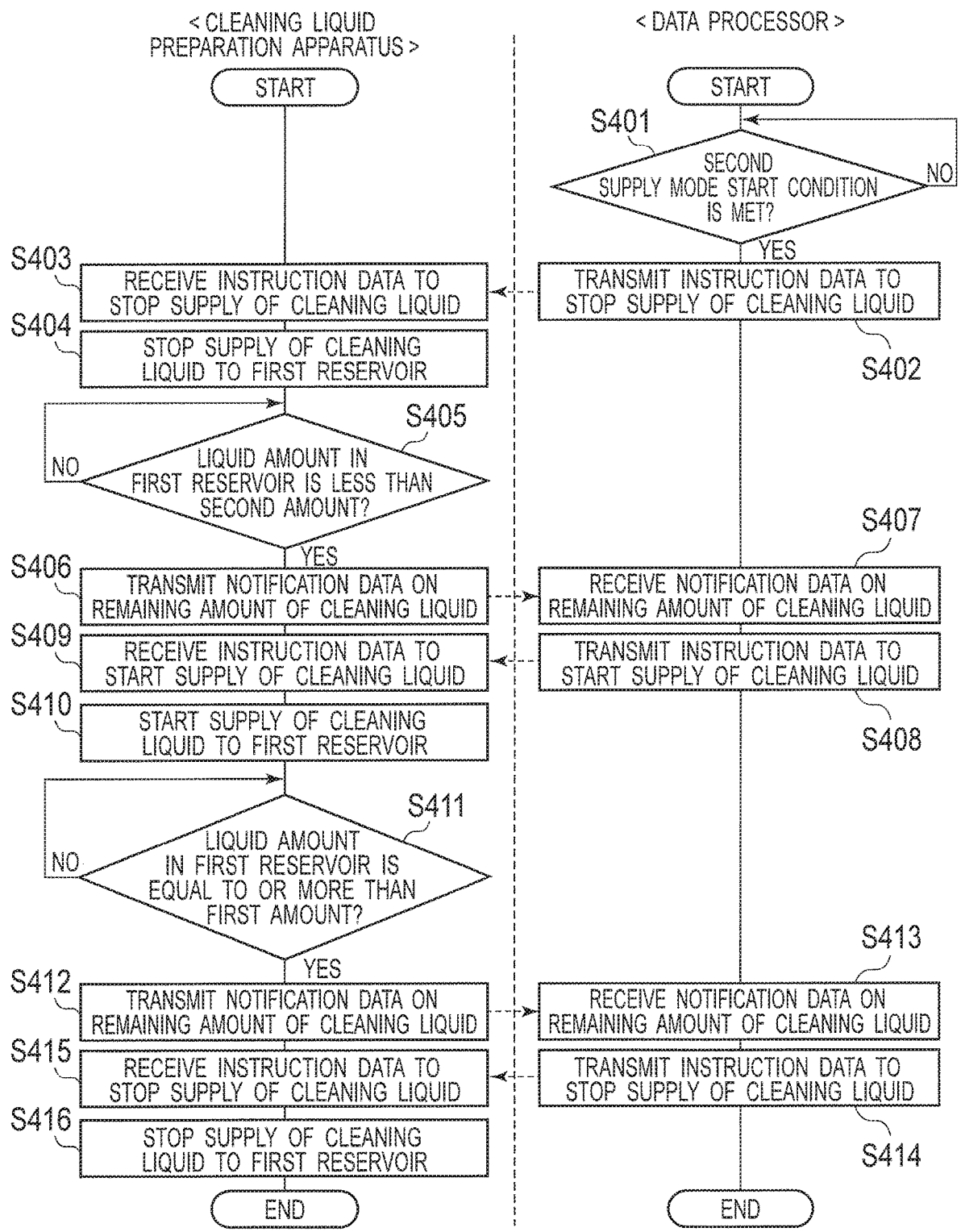
FIG. 10 is a flowchart illustrating procedures of a second supply mode in Embodiment 1.

With reference to FIG. 10, the second supply mode is specifically described.

CPU 301 determines whether or not the second supply mode start condition is met (Step S401). In the case where the second supply mode start condition is set to the wake-up of sample analyzer 1, CPU 301 determines that the second supply mode start condition is met when the communication with cleaning liquid preparation apparatus 4 is established after sample analyzer 1 is activated by automatic wake-up or sample analyzer 1 is manually activated. Alternatively, in the case where the second supply mode start condition is set to the change of the date in data processor 3, CPU 301 determines that the second supply mode start condition is met when the date change time arrives. Alternatively, in the case where the second supply mode start condition is set to the arrival of the time previously set by the user, CPU 301 determines that the second supply mode start condition is met when the time specified by the user arrives.

When the second supply mode start condition is not met (NO in Step S401), CPU 301 repeats the processing of Step S401.

When the second supply mode start condition is met (YES in Step S401), CPU 301 transmits instruction data to instruct to stop the supply of the cleaning liquid to cleaning liquid preparation apparatus 4 (Step S402).

When cleaning liquid preparation apparatus 4 receives the instruction data to stop the supply of the cleaning liquid (Step S403), controller 48 stops the supply of the cleaning liquid to first reservoir 20 from second reservoir 46 (Step S404). Here, when no cleaning liquid is supplied to first reservoir 20 from second reservoir 46, cleaning liquid preparation apparatus 4 keeps on stopping the supply of the cleaning liquid to the first reservoir. On the other hand, when the cleaning liquid is supplied to first reservoir 20 from second reservoir 46, controller 48 closes supply part 427 to stop the supply of the cleaning liquid to the first reservoir.

Controller 48 determines whether or not the liquid amount in first reservoir 20 is less than the second amount, based on an output signal from second detector 22 (Step S405). When the liquid amount in first reservoir 20 is equal to or more than the second amount, that is, no detection signal is outputted from second detector 22 (NO in Step S405), controller 48 repeats the processing of Step S405.

Thus, in measurement unit 2, the cleaning liquid is consumed until the liquid amount falls below the second amount. The second amount is 3 L, and a large amount of old cleaning liquid is consumed.

When the liquid amount in first reservoir 20 is less than the second amount, that is, the detection signal is outputted from second detector 22 (YES in Step S405), controller 48 transmits notification data for notifying that the remaining amount of cleaning liquid is less than the second amount to data processor 3 (Step S406).

When data processor 3 receives the notification data on the remaining amount of cleaning liquid (Step S407), CPU 301 transmits instruction data to instruct to start the supply of the cleaning liquid to cleaning liquid preparation apparatus 4 (Step S408).

Figure 7C:
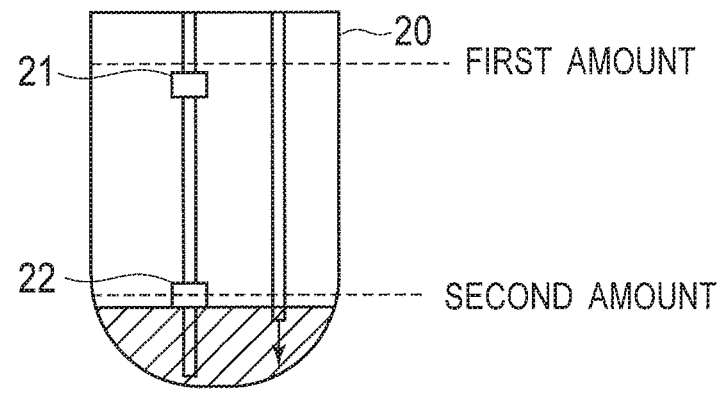
FIG. 7C is a diagram for explaining replacement of a cleaning liquid to the first reservoir.

When cleaning liquid preparation apparatus 4 receives the instruction data to start the supply of the cleaning liquid (Step S409), controller 48 opens supply part 427 to start the supply of the cleaning liquid to first reservoir 20 from second reservoir 46 (Step S410). As illustrated in FIG. 7C, when the liquid amount in first reservoir 20 falls below the second amount, the cleaning liquid is supplied to first reservoir 20. Since the cleaning liquid supplied to first reservoir 20 from second reservoir 46 is new, the old cleaning liquid is replaced with new cleaning liquid in first reservoir 20.

The cleaning liquid stored in first reservoir 20 is a cleaning liquid. Thus, even when a certain amount of old cleaning liquid is mixed with new cleaning liquid, the measurement of the sample is hardly affected thereby if the amount of the old cleaning liquid is small. With such a cleaning liquid having the remaining old cleaning liquid reduced as much as possible and having new cleaning liquid added thereto, the accuracy of sample measurement can be maintained while saving of the trouble of managing the cleaning liquid is achieved.

Moreover, the second amount can also be set to zero. In this case, all the old cleaning liquid can be replaced with new cleaning liquid.

Next, controller 48 determines whether or not the liquid amount in first reservoir 20 is equal to or more than the first amount, based on the output signal from first detector 21 (Step S411). When the liquid amount in first reservoir 20 is less than the first amount, that is, the detection signal is outputted from first detector 21 (NO in Step S411), controller 48 repeats the processing of Step S411. Thus, the supply of the cleaning liquid from second reservoir 46 to first reservoir 20 is carried on.

When the liquid amount in first reservoir 20 reaches the first amount or more, that is, no more detection signal is outputted from first detector 21 (YES in Step S411), controller 48 transmits notification data for notifying that the remaining amount of cleaning liquid reaches the first amount or more to data processor 3 (Step S412).

When data processor 3 receives the notification data on the remaining amount of cleaning liquid (Step S413), CPU 301 transmits instruction data to instruct to stop the supply of the cleaning liquid to cleaning liquid preparation apparatus 4 (Step S414), and then terminates the processing.

When cleaning liquid preparation apparatus 4 receives the instruction data to stop the supply of the cleaning liquid (Step S415), controller 48 closes supply part 427 to stop the supply of the cleaning liquid to first reservoir 20 from second reservoir 46 (Step S416), and then terminates the processing. As illustrated in FIG. 7B, when the liquid amount in first reservoir 20 reaches the first amount or more, the supply of the cleaning liquid to first reservoir 20 is stopped. By supplying new cleaning liquid in the first amount or more, such large amount of new cleaning liquid can be stored in the reservoir. Note that the cleaning liquid need not be supplied equal to or more than the first amount in first reservoir 20. For example, the supply of the cleaning liquid to first reservoir 20 may be stopped at a third amount between the first amount and the second amount. Alternatively, the cleaning liquid may be supplied equal to or more than a fourth amount greater than the first amount in first reservoir 20, and the supply of the cleaning liquid may be stopped when the liquid amount reaches the fourth amount or more.

Note that, when the liquid amount in first reservoir 20 falls below the second amount, controller 48 may open supply part 427 to supply the cleaning liquid to first reservoir 20 from second reservoir 46 without sending notification data to data processor 3. On the other hand, when the liquid amount in first reservoir 20 reaches the first amount or more, controller 48 may close supply part 427 to stop the supply of the cleaning liquid to first reservoir 20 from second reservoir 46 without sending notification data to data processor 3.

In the second supply mode, when the liquid amount in first reservoir 20 falls below the second amount (about 3 L), the supply of the cleaning liquid to first reservoir 20 is started. More specifically, the liquid amount in first reservoir 20 is less than the first amount by about 6 L at the start of the supply of the cleaning liquid to first reservoir 20. Moreover, since the cleaning liquid is supplied until the liquid amount in first reservoir 20 reaches the first amount or more, the amount of cleaning liquid to be supplied is about 6 L. Therefore, in the second supply mode, when the liquid amount in first reservoir 20 falls below the second amount (about 3 L), the cleaning liquid in an amount more than the second amount is supplied to first reservoir 20.

With the configuration as described above, the old cleaning liquid in first reservoir 20 can be replaced with new cleaning liquid without discarding the cleaning liquid in first reservoir 20.

Moreover, the second supply mode as described above may be consecutively executed twice or more. Thus, the amount of old cleaning liquid can be further reduced. In addition, cleaning liquid preparation apparatus 4, in the second supply mode, may discard the cleaning liquid stored in second reservoir 46, store newly prepared cleaning liquid in second reservoir 46, suspends start of supply of the cleaning liquid to first reservoir 20 until the liquid amount in first reservoir 20 reaches the second amount, and then supplies the cleaning liquid to first reservoir 20 when the liquid amount in the reservoir falls below the second amount.

In the second supply mode, the amount of the cleaning liquid in first reservoir 20 is not reduced so much below the second amount. If there is the second amount of cleaning liquid in first reservoir 20, at least measurement of the sample that is being measured can be completed. Moreover, the sample measurement can be carried on by supplying new cleaning liquid during the measurement of the sample.

Embodiment 2

In this embodiment, description is given of a sample analysis system in which a data processor controls a cleaning liquid preparation apparatus to supply a cleaning liquid to a first reservoir from a second reservoir.

First and second detectors 21 and 22 are not connected to controller 48, but are connected to input-output interface 306 in data processor 3. Each of first and second detectors 21 and 22 outputs a detection signal to data processor 3.

Note that the other configuration of the sample analysis system according to this embodiment is the same as that of sample analysis system 100 according to Embodiment 1. Therefore, the same constituent components are denoted by the same reference numerals, and description thereof is omitted.

<First Supply Mode>

Figure 11:
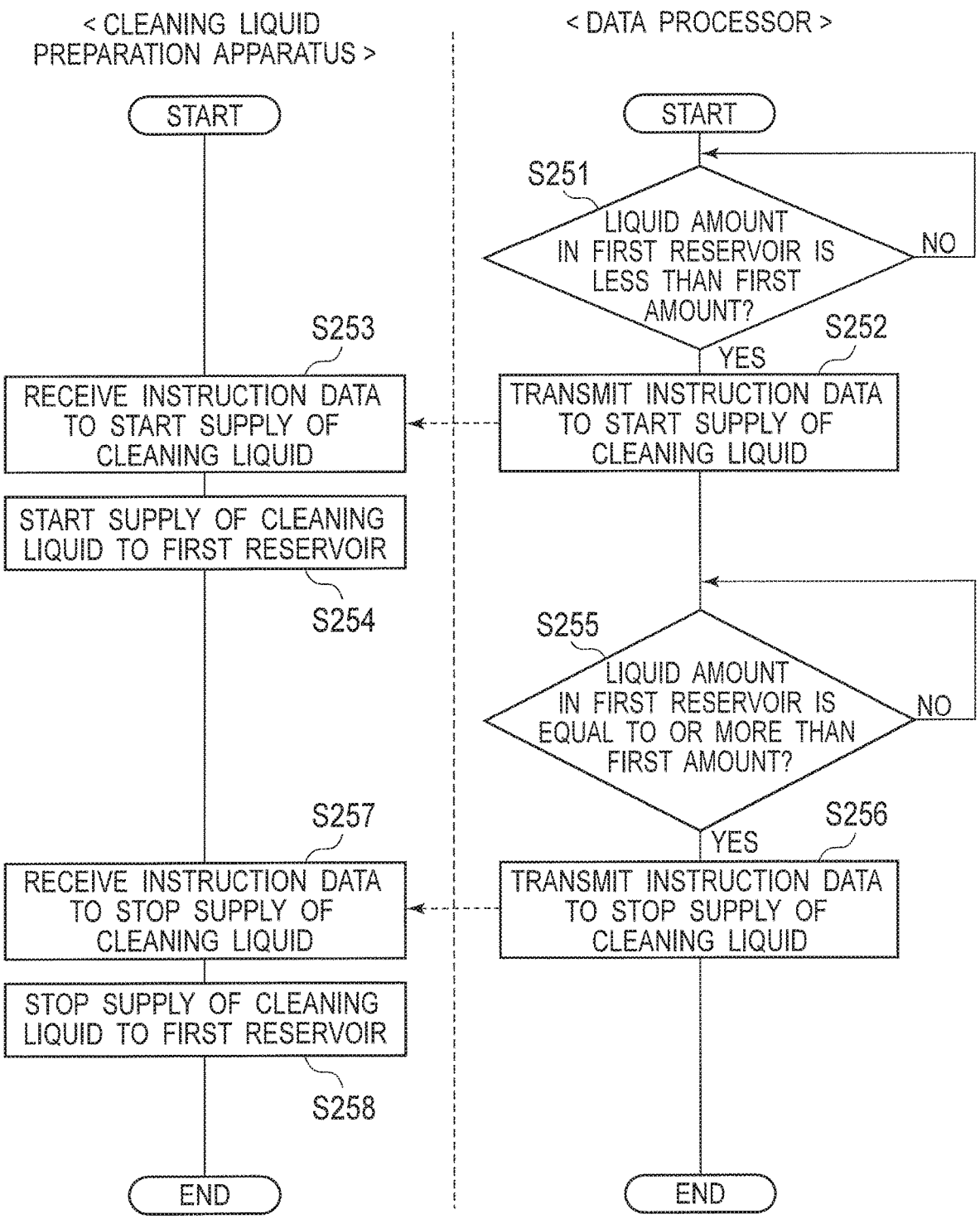
FIG. 11 is a flowchart illustrating procedures of a first supply mode in Embodiment 2.

With reference to FIG. 11, a first supply mode is described.

In the first supply mode, CPU 301 determines whether or not the liquid amount in first reservoir 20 is less than a first amount, based on an output signal from first detector 21 (Step S251). When the liquid amount in first reservoir 20 is equal to or more than the first amount, that is, no detection signal is outputted from first detector 21 (NO in Step S251), CPU 301 repeats the processing of Step S251.

When the liquid amount in first reservoir 20 is less than the first amount, that is, the detection signal is outputted from first detector 21 (YES in Step S251), CPU 301 transmits instruction data to instruct to start the supply of the cleaning liquid to first reservoir 20 to cleaning liquid preparation apparatus 4 (Step S252).

When cleaning liquid preparation apparatus 4 receives the instruction data to start the supply of the cleaning liquid (Step S253), controller 48 opens supply part 427 to start the supply of the cleaning liquid to first reservoir 20 from second reservoir 46 (Step S254).

CPU 301 determines whether or not the liquid amount in first reservoir 20 is equal to or more than the first amount, based on the output signal from first detector 21 (Step S255). When the liquid amount in first reservoir 20 is less than the first amount, that is, the detection signal is outputted from first detector 21 (NO in Step S255), CPU 301 repeats the processing of Step S255. Thus, the supply of the cleaning liquid from second reservoir 46 to first reservoir 20 is carried on.

When the liquid amount in first reservoir 20 reaches equal to or more than the first amount, that is, no more detection signal is outputted from first detector 21 (YES in Step S255), CPU 301 transmits instruction data to instruct to stop the supply of the cleaning liquid to cleaning liquid preparation apparatus 4 (Step S256), and then terminates the processing.

When cleaning liquid preparation apparatus 4 receives the instruction data to stop the supply of the cleaning liquid (Step S257), controller 48 closes supply part 427 to stop the supply of the cleaning liquid to first reservoir 20 from second reservoir 46 (Step S258), and then terminates the processing.

<Second Supply Mode>

Figure 12:
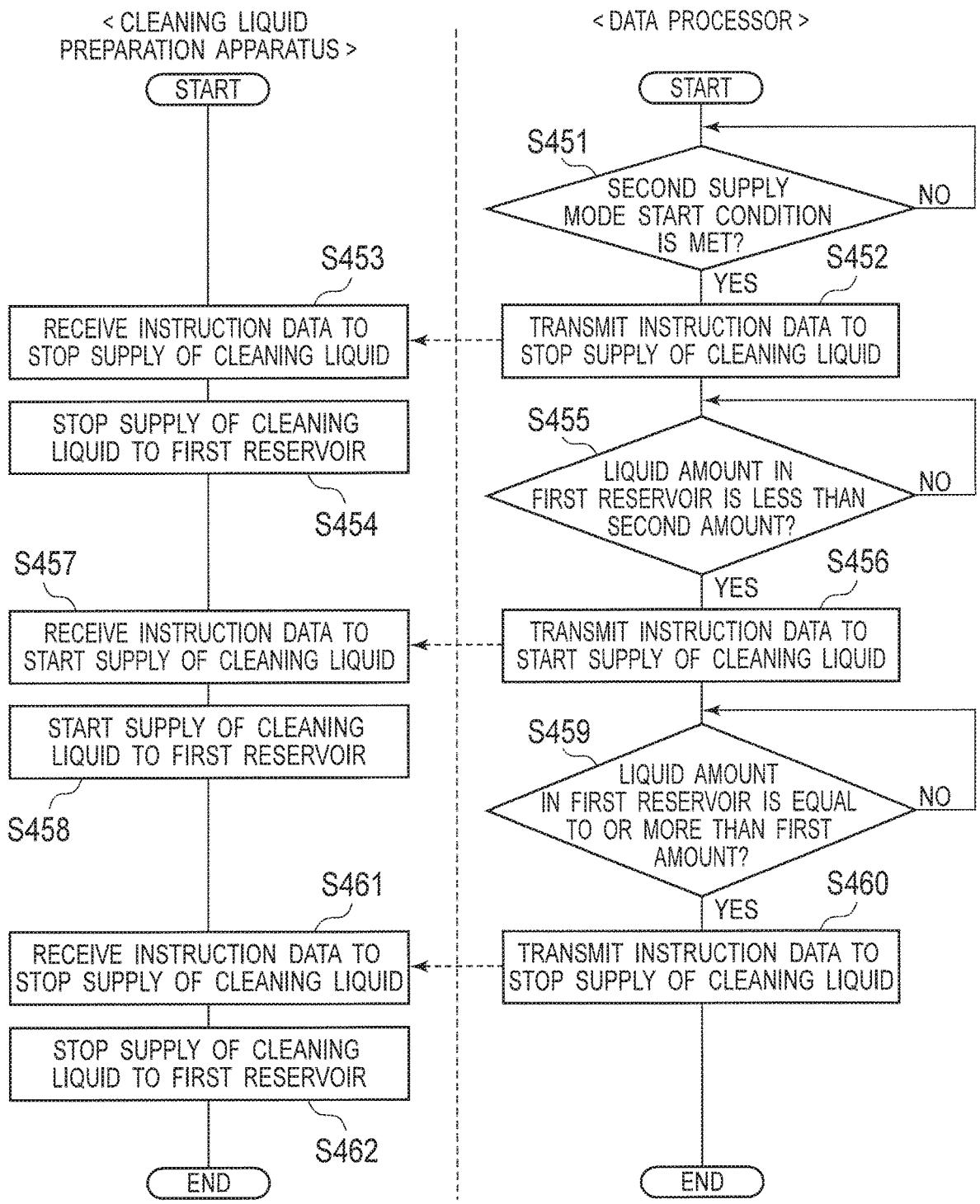
FIG. 12 is a flowchart illustrating procedures of a second supply mode in Embodiment 2.

With reference to FIG. 12, a second supply mode is described.

CPU 301 determines whether or not the second supply mode start condition is met (Step S451). The processing of Step S451 is the same as the processing of Step S401 in Embodiment 1.

When the second supply mode start condition is not met (NO in Step S451), CPU 301 repeats the processing of Step S451.

When the second supply mode start condition is met (YES in Step S451), CPU 301 transmits instruction data to instruct to stop the supply of the cleaning liquid to cleaning liquid preparation apparatus 4 (Step S452).

When cleaning liquid preparation apparatus 4 receives the instruction data to stop the supply of the cleaning liquid (Step S453), controller 48 stops the supply of the cleaning liquid to first reservoir 20 from second reservoir 46 (Step S454).

CPU 301 determines whether or not the liquid amount in first reservoir 20 is less than a second amount, based on an output signal from second detector 22 (Step S455). When the liquid amount in first reservoir 20 is equal to or more than the second amount, that is, no detection signal is outputted from second detector 22 (NO in Step S455), CPU 301 repeats the processing of Step S455.

Thus, in measurement unit 2, the cleaning liquid is consumed until the liquid amount falls below the second amount. The second amount is 3 L, and a large amount of old cleaning liquid is consumed.

When the liquid amount in first reservoir 20 is less than the second amount, that is, the detection signal is outputted from second detector 22 (YES in Step S455), CPU 301 transmits instruction data to instruct to start the supply of the cleaning liquid to cleaning liquid preparation apparatus 4 (Step S456).

When cleaning liquid preparation apparatus 4 receives the instruction data to start the supply of the cleaning liquid (Step S457), controller 48 opens supply part 427 to start the supply of the cleaning liquid to first reservoir 20 from second reservoir 46 (Step S458).

Next, CPU 301 determines whether or not the liquid amount in first reservoir 20 is equal to or more than the first amount, based on the output signal from first detector 21 (Step S459). When the liquid amount in first reservoir 20 is less than the first amount, that is, the detection signal is outputted from first detector 21 (NO in Step S459), CPU 301 repeats the processing of Step S459. Thus, the supply of the cleaning liquid from second reservoir 46 to first reservoir 20 is carried on.

When the liquid amount in first reservoir 20 reaches the first amount or more, that is, no more detection signal is outputted from first detector 21 (YES in Step S459), CPU 301 transmits instruction data to instruct to stop the supply of the cleaning liquid to cleaning liquid preparation apparatus 4 (Step S460).

When cleaning liquid preparation apparatus 4 receives the instruction data to stop the supply of the cleaning liquid (Step S461), controller 48 closes supply part 427 to stop the supply of the cleaning liquid to first reservoir 20 from second reservoir 46 (Step S462), and then terminates the processing.

Embodiment 3

In this embodiment, description is given of a sample analyzer which supplies a cleaning liquid to a reservoir provided in a measurement unit from a cleaning liquid container connected to the measurement unit.

Figure 13:
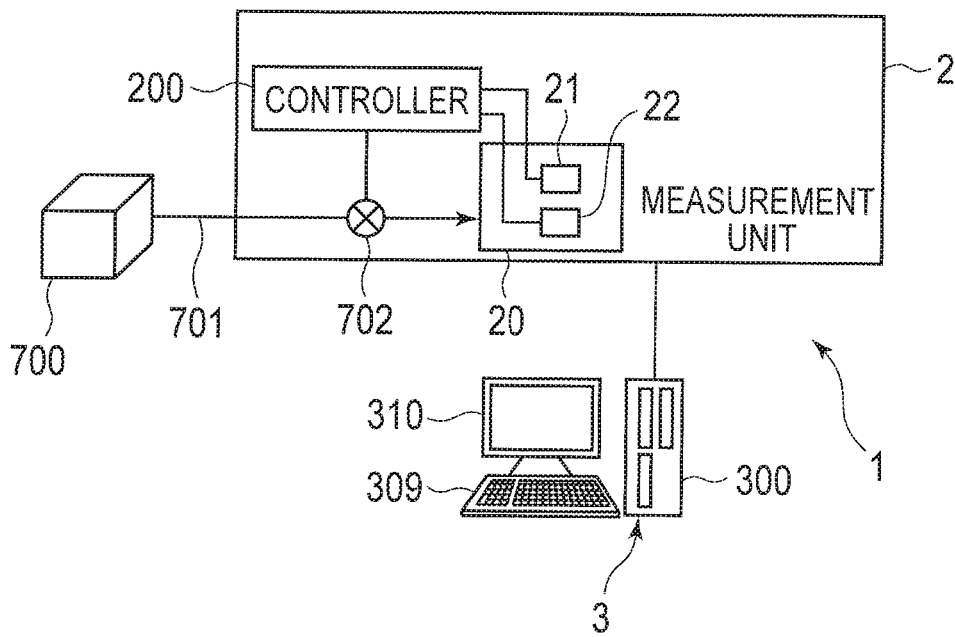
FIG. 13 is a schematic diagram illustrating a configuration of a sample analyzer according to Embodiment 3.

With reference to FIG. 13, sample analyzer 1 includes measurement unit 2 and data processor 3. Measurement unit 2 is connected to cleaning liquid container 700 that houses the cleaning liquid to be used for cleaning of measurement unit 2. Measurement unit 2 includes first reservoir 20, and first reservoir 20 is connected to cleaning liquid container 700 through flow path 701. Flow path 701 is provided with electromagnetic valve 702. When electromagnetic valve 702 is opened, the cleaning liquid is sent from cleaning liquid container 700 and supplied to first reservoir 20 through flow path 701. When electromagnetic valve 702 is closed, the supply of the cleaning liquid to first reservoir 20 is stopped.

Controller 200 in measurement unit 2 is connected so as to be able to control electromagnetic valve 702. Also, controller 200 is connected to first and second detectors 21 and 22. Each of first and second detectors 21 and 22 outputs a detection signal to controller 200.

Note that the other configuration of sample analyzer 1 according to this embodiment is the same as that of sample analyzer 1 according to Embodiment 1. Therefore, the same constituent components are denoted by the same reference numerals, and description thereof is omitted.

<First Supply Mode>

With the consumption of the cleaning liquid, measurement unit 2 executes a first supply mode as described below.

Figure 14:
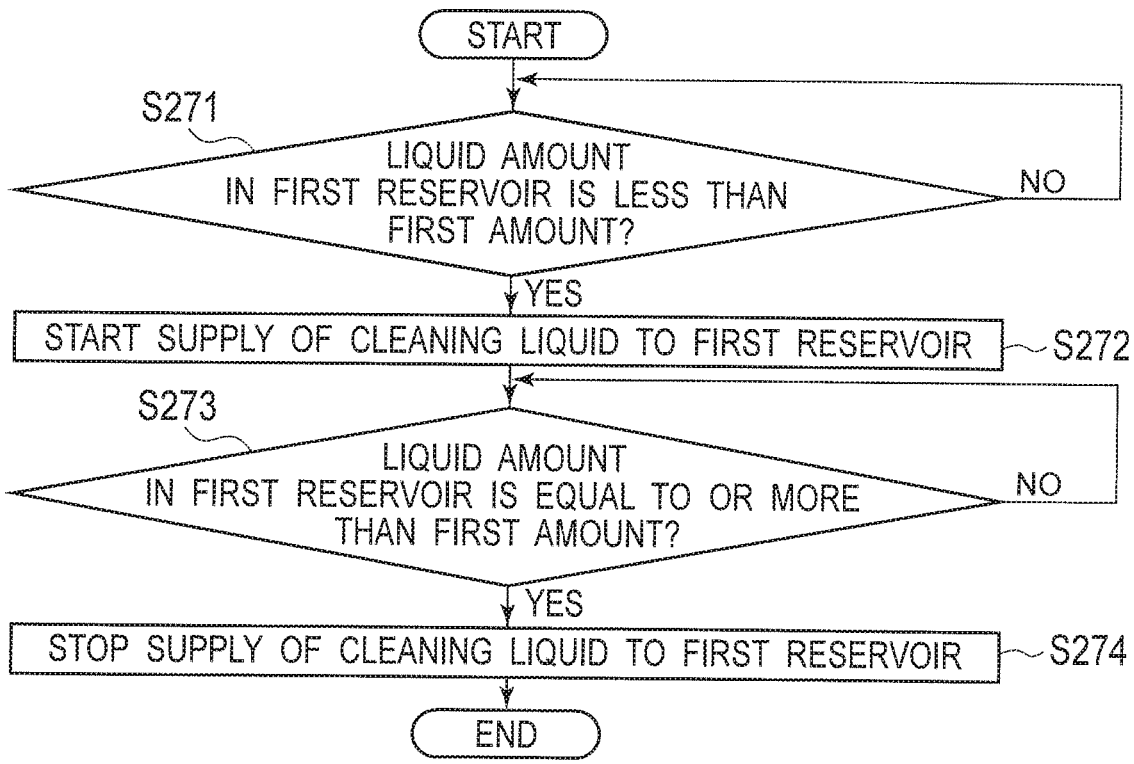
FIG. 14 is a flowchart illustrating procedures of a first supply mode in Embodiment 3.

With reference to FIG. 14, the first supply mode is described.

In the first supply mode, controller 200 determines whether or not the liquid amount in first reservoir 20 is less than a first amount, based on an output signal from first detector 21 (Step S271). When the liquid amount in first reservoir 20 is equal to or more than the first amount, that is, no detection signal is outputted from first detector 21 (NO in Step S271), controller 200 repeats the processing of Step S271.

When the liquid amount in first reservoir 20 is less than the first amount, that is, the detection signal is outputted from first detector 21 (YES in Step S271), controller 200 opens electromagnetic valve 702 to start the supply of the cleaning liquid to first reservoir 20 (Step S272).

Controller 200 determines whether or not the liquid amount in first reservoir 20 is equal to or more than the first amount, based on the output signal from first detector 21 (Step S273). When the liquid amount in first reservoir 20 is less than the first amount, that is, the detection signal is outputted from first detector 21 (NO in Step S273), controller 200 repeats the processing of Step S273. Thus, the supply of the cleaning liquid to first reservoir 20 is carried on.

When the liquid amount in first reservoir 20 reaches the first amount or more, that is, no more detection signal is outputted from first detector 21 (YES in Step S273), controller 200 closes electromagnetic valve 702 to stop the supply of the cleaning liquid to first reservoir 20 (Step S274), and then terminates the processing.

Measurement unit 2 can maintain the liquid amount in first reservoir 20 at the first amount (about 9 L) by repeatedly executing the supply of the cleaning liquid in the first supply mode as described above.

<Second Supply Mode>

With reference to FIG. 15, a second supply mode is specifically described.

CPU 301 determines whether or not the second supply mode start condition is met (Step S471). The processing of Step S471 is the same as the processing of Step S401 in Embodiment 1.

When the second supply mode start condition is not met (NO in Step S471), CPU 301 repeats the processing of Step S471.

When the second supply mode start condition is met (YES in Step S471), CPU 301 transmits instruction data to instruct to stop the supply of the cleaning liquid to measurement unit 2 (Step S472).

When measurement unit 2 receives the instruction data to stop the supply of the cleaning liquid (Step S473), controller 200 stops the supply of the cleaning liquid to first reservoir 20 from cleaning liquid container 700 (Step S474). Here, when no cleaning liquid is supplied to first reservoir 20 from cleaning liquid container 700, measurement unit 2 keeps on stopping the supply of the cleaning liquid to first reservoir 20. On the other hand, when the cleaning liquid is supplied to first reservoir 20 from cleaning liquid container 700, controller 200 closes electromagnetic valve 702 to stop the supply of the cleaning liquid to first reservoir 20.

Controller 200 determines whether or not the liquid amount in first reservoir 20 is less than a second amount, based on an output signal from second detector 22 (Step S475). When the liquid amount in first reservoir 20 is equal to or more than the second amount, that is, no detection signal is outputted from second detector 22 (NO in Step S475), controller 200 repeats the processing of Step S475.

Thus, in measurement unit 2, the cleaning liquid is consumed until the liquid amount falls below the second amount. The second amount is 3 L, and a large amount of old cleaning liquid is consumed.

When the liquid amount in first reservoir 20 is less than the second amount, that is, the detection signal is outputted from second detector 22 (YES in Step S475), controller 200 opens electromagnetic valve 702 to start the supply of the cleaning liquid to first reservoir 20 (Step S476).

Next, controller 200 determines whether or not the liquid amount in first reservoir 20 is equal to or more than the first amount, based on the output signal from first detector 21 (Step S477). When the liquid amount in first reservoir 20 is less than the first amount, that is, the detection signal is outputted from first detector 21 (NO in Step S477), controller 200 repeats the processing of Step S477. Thus, the supply of the cleaning liquid to first reservoir 20 from cleaning liquid container 700 is carried on.

When the liquid amount in first reservoir 20 reaches the first amount or more, that is, no more detection signal is outputted from first detector 21 (YES in Step S477), controller 200 closes electromagnetic valve 702 to stop the supply of the cleaning liquid to first reservoir 20 from cleaning liquid container 700 (Step S478), and then terminates the processing.

According to the embodiments described above, a prepared cleaning liquid can be stored after preparation thereof and, in the case of cleaning the sample analyzer with the stored cleaning liquid, the stored cleaning liquid can mainly contain newly prepared cleaning liquid. Also, the sample analyzer can be quickly cleaned with the stored cleaning liquid.

The invention includes other embodiments in addition to the above-described embodiments without departing from the spirit of the invention. The embodiments are to be considered in all respects as illustrative, and not restrictive. The scope of the invention is indicated by the appended claims rather than by the foregoing description. Hence, all configurations including the meaning and range within equivalent arrangements of the claims are intended to be embraced in the invention.

The invention claimed is:

1. A sample analysis system comprising:
   a cleaning liquid preparation apparatus that prepares a cleaning liquid; and
   a sample analyzer that:
      comprises a measurement unit that measures a sample and a first reservoir that stores the cleaning liquid prepared by the cleaning liquid preparation apparatus, and
      cleans at least a part of the measurement unit with the cleaning liquid,
   wherein
   the cleaning liquid preparation apparatus comprises a second reservoir that stores the prepared cleaning liquid,
   the first reservoir comprises first and second sensors,
      the first sensor being arranged to detect a level of liquid in the first reservoir at a first level, and
      the second sensor being arranged to detect a level of liquid in the first reservoir at a second level which is below the first level but is above a level at which the first reservoir is empty,
   the sample analysis system is programmed to operate selectively under a first supply mode and a second supply mode and to store, in a data storage device, a preset condition that triggers the second supply mode,
   the cleaning liquid preparation apparatus is configured, under the first supply mode, to supply the cleaning liquid to the first reservoir, when the first sensor detects that the level falls below the first level, so as to bring the level above the first level, and
   the cleaning liquid preparation apparatus is configured to operate under the second supply mode in response to the preset condition being met, to let the cleaning liquid in the first reservoir be consumed by keeping a valve between the first reservoir and the second reservoir of the cleaning liquid preparation apparatus closed until the second sensor detects that the level falls below the second level and then open the valve to supply the cleaning liquid to the first reservoir,
   the sample analysis system further comprises a data processor that processes measurement data obtained through measurement by the measurement unit, and
   the preset condition comprises: that communication between the data processor and the cleaning liquid preparation apparatus is established; that a date of an internal clock provided in the data processor changes to a next date; or that a preset time arrives.

2. The sample analysis system according to claim 1, wherein the cleaning liquid preparation apparatus is configured to operate under the first supply mode and to switch to operate under the second supply mode when the preset condition is met.

3. The sample analysis system according to claim 1, wherein the measurement unit comprises a reagent dispenser with a probe to dispense a reagent for measurement of the sample, and the measurement unit cleans the probe with the cleaning liquid.

4. The sample analysis system according to claim 1, wherein
the cleaning liquid preparation apparatus is configured to supply a larger amount of liquid than that remaining in the first reservoir under the second supply mode so that the newly supplied amount of liquid comprises a majority of the liquid in the first reservoir.

5. The sample analysis system according to claim 1, wherein the cleaning liquid preparation apparatus comprises:
a supply unit that supplies the prepared cleaning liquid to the first reservoir, and
a controller that controls the supply unit.

6. The sample analysis system according to claim 1, further comprising:
a data processor that processes measurement data obtained through measurement by the measurement unit and controls an operation of the cleaning liquid preparation apparatus.

7. The sample analysis system according to claim 3, wherein
the cleaning liquid preparation apparatus supplies the cleaning liquid to the first reservoir from the second reservoir, and
the cleaning liquid preparation apparatus, in the second supply mode, discards the cleaning liquid stored in the second reservoir, stores newly prepared cleaning liquid in the second reservoir, suspends start of supply of the cleaning liquid to the first reservoir until the level reaches the second level, and then supplies the cleaning liquid to the first reservoir when the level falls below the second level with the sample analyzer using the cleaning liquid in the first reservoir to clean the probe.

8. The sample analysis system according to claim 2, wherein the preset condition is that the cleaning liquid preparation apparatus is activated.

9. The sample analysis system according to claim 1, further comprising a data processor that processes measurement data obtained through measurement by the measurement unit, wherein
the data processor comprises a display unit through which a user inputs the preset condition.

10. The sample analysis system according to claim 1, wherein the measurement unit is capable of measuring a blood sample immunologically.

11. The sample analysis system according to claim 10, wherein
the measurement unit further includes a B/F separator that separates magnetic particles carrying capture antibodies, which are capable of being bound to antigens contained in the blood sample, from unwanted components, after the magnetic particles are added to a reaction chamber that houses the blood sample, and the B/F separator cleans the magnetic particles in the reaction chamber with a cleaning liquid different from the cleaning liquid.

12. The sample analysis system according to claim 1, wherein the cleaning liquid preparation apparatus comprises a flow path through which the cleaning liquid flows, and a pump connected to the flow path, and supplies the cleaning liquid to the first reservoir through the flow path.

13. A sample analysis system comprising:
a cleaning liquid preparation apparatus that prepares a cleaning liquid;
a sample analyzer; and
a data processor comprising a display,
wherein the sample analyzer comprises a measurement unit that measures a sample and a reservoir that stores the cleaning liquid prepared by the cleaning liquid preparation apparatus and cleans at least a part of the measurement unit with the cleaning liquid,
wherein the cleaning liquid preparation apparatus comprises a first sensor and a second sensor, the first sensor being arranged to detect a level of liquid in the reservoir at a first level, and the second sensor being arranged to detect a level of liquid in the reservoir at a second level which is below the first level but is above a level at which the reservoir is empty,
wherein the sample analysis system is programmed to operate selectively under a first supply mode and a second supply mode,
wherein the data processor is programmed to show a condition setting screen, on the display, which selectably presents options including at least a first condition and a second condition to be set to trigger the second supply mode,
the cleaning liquid preparation apparatus is configured, under the first supply mode, to supply the cleaning liquid to the reservoir, when the first sensor detects that the level falls below the first level, so as to bring the level above the first level, and
the cleaning liquid preparation apparatus is configured to operate under the second supply mode, to stop a replenishment of the cleaning liquid to the reservoir until the second sensor detects that the level falls below the second level by a consumption of the cleaning liquid and then start the replenishment of the cleaning liquid to the reservoir,
the data processor processes measurement data obtained through measurement by the measurement unit, and
at least one of the first condition and the second condition comprises: that communication between the data processor and the cleaning liquid preparation apparatus is established; that a date of an internal clock provided in the data processor changes to a next date; or that a preset time arrives.

* * * * *